United States Patent [19]
Selden et al.

[11] Patent Number: 6,083,725
[45] Date of Patent: Jul. 4, 2000

[54] TRANFECTED HUMAN CELLS EXPRESSING HUMAN α-GALACTOSIDASE A PROTEIN

[75] Inventors: Richard F. Selden, Wellesley; Marianne Borowski, Winthrop; Frances P. Gillispie, Lexington; Carol M. Kinoshita, Bedford; Douglas A. Treco, Arlington; Melanie D. Williams, Natick, all of Mass.

[73] Assignee: Transkaryotic Therapies, Inc., Cambridge, Mass.

[21] Appl. No.: 08/928,881

[22] Filed: Sep. 12, 1997

Related U.S. Application Data

[60] Provisional application No. 60/026,041, Sep. 13, 1996.
[51] Int. Cl.$^7$ ............................... C12N 5/10; C12N 5/08; C12N 9/40; C12P 21/02
[52] U.S. Cl. ..................... 435/69.8; 435/208; 435/320.1; 435/366; 435/367; 435/368; 435/369; 435/370; 435/371; 435/372; 435/372.1; 435/372.2; 435/372.3; 435/455; 536/23.2; 536/23.4
[58] Field of Search ................................ 536/23.4, 23.2; 435/366, 367, 368, 369, 370, 371, 372, 372.1, 372.2, 372.3, 320.1, 455, 69.8, 208

[56] References Cited

U.S. PATENT DOCUMENTS

| | | | |
|---|---|---|---|
| 5,179,023 | 1/1993 | Calhoun et al. | 435/235.1 |
| 5,356,804 | 10/1994 | Desnick et al. | 435/208 |
| 5,401,650 | 3/1995 | Desnick et al. | 435/208 |
| 5,661,132 | 8/1997 | Eriksson et al. | 514/44 |

FOREIGN PATENT DOCUMENTS

| | | |
|---|---|---|
| 21796/88 | 9/1988 | Australia . |
| 0 307 285 | 3/1989 | European Pat. Off. . |
| WO 90/11353 | 10/1990 | WIPO . |
| WO 93/09222 | 5/1993 | WIPO . |
| WO 94/12628 | 6/1994 | WIPO . |
| WO 95/06478 | 3/1995 | WIPO . |

OTHER PUBLICATIONS

Pecceu et al., Gene 97:253–258 (1991).

Ashwell et al., "Carbohydrate–Specific Receptors of the Liver" Ann. Rev. Biochem. 51:531–554, 1982.

Bishop, David et al., "Enzyme Therapy XX: Further Evidence for the Differential In Vivo Fate of Human Splenic and Plasma . . . ," In Lysosomes and Lysosomal Storage Disease, Raven Press, NY, 1981, pp. 381–394.

Bishop et al., Proc. Natl. Acad. Sci. USA 83:4859, 1986; "Human α–galactosidase A: Nucleotide sequence of a cDNA clone encoding the mature enzyme".

Bishop et al., J. Biol. Chem. 256:1307–1316, 1981; "Affinity Purification of α–Galactosidase A from Human Spleen, Placenta, and Plasma with Elimination of Pyrogen Contamination".

Brady et al., N. Engl. J. Med. 289:9, 1973; "Replacement Therapy for Inherited Enzyme Deficiency".

Desnick et al., Proc. Natl. Acad. Sci. USA 76:5326, 1979; "Enzyme therapy in Fabry disease: Differential in vivo plasma clearance and metabolic effectiveness of plasma and splenic α–galactosidase A isozymes".

Ioannou et al., J. Cell Biol. 119:1137, 1992; "Overexpression of Human α–galactosidase A results in its Intracellular Aggregation, Crystallization in Lysosomes and Selective Secretion".

Kornreich et al., Nucleic Acids Research; 17:3301, 1988.

Lemansky et al., J. Biol. Chem. 262:2062, 1987; "Synthesis and Processing of α–Galactosidase A in Human Fibroblasts".

Mapes et al., Science 169:987, 1970; "Enzyme Replacement in Fabry's Disease an Inborn Error of Metabolism".

Selden et al., Mol. Cell. Biol. 6:3173–3179, 1986; "Human Growth Hormone as a Reporter Gene in Regulation Studies Employing Transient Gene Expression".

Shrine, "TKT Files for IPO to Raise $35M as it Nears Human Testing," BioWorld Today, The Daily Biotechnology Newspaper, vol. 7, No. 170, 1996.

Tsuji et al., Eur. J. Biochem. 165:275, 1987; "Signal sequence and DNA–mediated expression of human lysosomal α–galactosidase A".

Medin, J.A. et al., *Proc. Natl. Acad. Sci. USA*, 93(15): 7917–7922 (1996).

PCT/US97/16603, search report.

*Primary Examiner*—Johnny F. Railey, II
*Attorney, Agent, or Firm*—Fish & Richardson P.C.

[57] ABSTRACT

A therepeutic method whereby an individual suspected of having an α-galactosidase A deficiency, such as Fabry disease, is treated either with (1) human cells that have been genetically modified to overexpress and secrete human α-gal A, or (2) purified human α-gal A obtained from cultured, genetically modified human cells.

37 Claims, 11 Drawing Sheets

CTGGGCTGTAGCTATGATAAACCGGCAGGA

GATTGGTGGACCTCGCTCTTATACCATCGCA

GTTGCTTCCCTGGGTAAAGGAGTGGCCTGTA

ATCCTGCCTGCTTCATCACACAGCTCCTCCCT

GTGAAAAGGAAGCTAGGGTTCTATGAATGGA

CTTCAAGGTTAAGAAGTCACATAAATCCCAC

AGGCACTGTTTTGCTTCAGCTAGA

FIG. 1

ATTGGTCCGCCCCTGAGGTTAATCTTAAAAG

SacII
CCCAGGTTACCCGCGGAAATTTATGCTGTC

CGGTCACCGTGACAATGCAGCTGAGGAACC

CAGAACTACATCTGGGCTGCGCGCTTGCGCT

TCGCTTCCTGGCCCTCGTTTCCTGGGACATC

CCTGGGGCTAGAGCACTGGACAATGGATTG

NcoI
GCAAGGACGCCACCATGGGCTGGCTGCAC

TGGGAGCGCTTCATGTGCAACCTTGACTGCC

AGGAAGAGCCAGATTCCTGCATCA

FIG. 2

```
   1 CCGCGGGAAA TTTATGCTGT CCGGTCACCG TGACAATGCA GCTGAGGAAC CCAGAACTAC
  61 ATCTGGGCTG CGCGCTTGCG CTTCGCTTCC TGGCCCTCGT TTCCTGGGAC ATCCCTGGGG
 121 CTAGAGCACT GGACAATGGA TTGGCAAGGA CGCCTACCAT GGGCTGGCTG CACTGGGAGC
 181 GCTTCATGTG CAACCTTGAC TGCCAGGAAG AGCCAGATTC CTGCATCAGT GAGAAGCTCT
 241 TCATGGAGAT GGCAGAGCTC ATGGTCTCAG AAGGCTGGAA GGATGCAGGT TATGAGTACC
 301 TCTGCATTGA TGACTGTTGG ATGGCTCCCC AAAGAGATTC AGAAGGCAGA CTTCAGGCAG
 361 ACCCTCAGCG CTTTCCTCAT GGGATTCGCC AGCTAGCTAA TTATGTTCAC AGCAAAGGAC
 421 TGAAGCTAGG GATTTATGCA GATGTTGGAA ATAAAACCTG CGCAGGCTTC CCTGGGAGTT
 481 TTGGATACTA CGACATTGAT GCCCAGACCT TGCTGACTG GGGAGTAGAT CTGCTAAAAT
 541 TTGATGGTTG TTACTGTGAC AGTTTGGAAA ATTTGGCAGA TGGTTATAAG CACATGTCCT
 601 TGGCCCTGAA TAGGACTGGC AGAAGCATTG TGTACTCCTG TGAGTGGCCT CTTTATATGT
 661 GGCCCTTTCA AAAGCCCAAT TATACAGAAA TCCGACAGTA CTGCAATCAC TGGCGAAATT
 721 TTGCTGACAT TGATGATTCC TGGAAAAGTA TAAAGAGTAT CTTGGACTGG ACATCTTTTA
 781 ACCAGGAGAG AATTGTTGAT GTTGCTGGAC CAGGGGGTTG GAATGACCCA GATATGTTAG
 841 TGATTGGCAA CTTTGGCCTC AGCTGGAATC AGCAAGTAAC TCAGATGGCC CTCTGGGCTA
 901 TCATGGCTGC TCCTTTATTC ATGTCTAATG ACCTCCGACA CATCAGCCCT CAAGCCAAAG
 961 CTCTCCTTCA GGATAAGGAC GTAATTGCCA TCAATCAGGA CCCCTTGGGC AAGCAAGGGT
1021 ACCAGCTTAG ACAGGGAGAC AACTTTGAAG TGTGGGAACG ACCTCTCTCA GGCTTAGCCT
1081 GGGCTGTAGC TATGATAAAC CGGCAGGAGA TTGGTGGACC TCGCTCTTAT ACCATCGCAG
1141 TTGCTTCCCT GGGTAAAGGA GTGGCCTGTA ATCCTGCCTG CTTCATCACA CAGCTCCTCC
1201 CTGTGAAAAG GAAGCTAGGG TTCTATGAAT GGACTTCAAG GTTAAGAAGT CACATAAATC
1261 CCACAGGCAC TGTTTTGCTT CAGCTAGAAA ATACAATGCA GATGTCATTA AAAGACTTAC
1321 TTTAAAAAAA AAAAAAACTC GAG
```

FIG. 3

| | | | | | | | | | | |
|---|---|---|---|---|---|---|---|---|---|---|
| Leu | Asp | Asn | Gly | Leu | Ala | Arg | Thr | Pro | Thr | Met | Gly |
| Trp | Leu | His | Trp | Glu | Arg | Phe | Met | Cys | Asn | Leu | Asp |
| Cys | Gln | Glu | Glu | Pro | Asp | Ser | Cys | Ile | Ser | Glu | Lys |
| Leu | Phe | Met | Glu | Met | Ala | Glu | Leu | Met | Val | Ser | Glu |
| Gly | Trp | Lys | Asp | Ala | Gly | Tyr | Glu | Tyr | Leu | Cys | Ile |
| Asp | Asp | Cys | Trp | Met | Ala | Pro | Gln | Arg | Asp | Ser | Glu |
| Gly | Arg | Leu | Gln | Ala | Asp | Pro | Gln | Arg | Phe | Pro | His |
| Gly | Ile | Arg | Gln | Leu | Ala | Asn | Tyr | Val | His | Ser | Lys |
| Gly | Leu | Lys | Leu | Gly | Ile | Tyr | Ala | Asp | Val | Gly | Asn |
| Lys | Thr | Cys | Ala | Gly | Phe | Pro | Gly | Ser | Phe | Gly | Tyr |
| Tyr | Asp | Ile | Asp | Ala | Gln | Thr | Phe | Ala | Asp | Trp | Gly |
| Val | Asp | Leu | Leu | Lys | Phe | Asp | Gly | Cys | Tyr | Cys | Asp |
| Ser | Leu | Glu | Asn | Leu | Ala | Asp | Gly | Tyr | Lys | His | Met |
| Ser | Leu | Ala | Leu | Asn | Arg | Thr | Gly | Arg | Ser | Ile | Val |
| Tyr | Ser | Cys | Glu | Trp | Pro | Leu | Tyr | Met | Trp | Pro | Phe |
| Gln | Lys | Pro | Asn | Tyr | Thr | Glu | Ile | Arg | Gln | Tyr | Cys |
| Asn | His | Trp | Arg | Asn | Phe | Ala | Asp | Ile | Asp | Asp | Ser |
| Trp | Lys | Ser | Ile | Lys | Ser | Ile | Leu | Asp | Trp | Thr | Ser |
| Phe | Asn | Gln | Glu | Arg | Ile | Val | Asp | Val | Ala | Gly | Pro |
| Gly | Gly | Trp | Asn | Asp | Pro | Asp | Met | Leu | Val | Ile | Gly |
| Asn | Phe | Gly | Leu | Ser | Trp | Asn | Gln | Gln | Val | Thr | Gln |
| Met | Ala | Leu | Trp | Ala | Ile | Met | Ala | Ala | Pro | Leu | Phe |
| Met | Ser | Asn | Asp | Leu | Arg | His | Ile | Ser | Pro | Gln | Ala |
| Lys | Ala | Leu | Leu | Gln | Asp | Lys | Asp | Val | Ile | Ala | Ile |
| Asn | Gln | Asp | Pro | Leu | Gly | Lys | Gln | Gly | Tyr | Gln | Leu |
| Arg | Gln | Gly | Asp | Asn | Phe | Glu | Val | Trp | Glu | Arg | Pro |
| Leu | Ser | Gly | Leu | Ala | Trp | Ala | Val | Ala | Met | Ile | Asn |
| Arg | Gln | Glu | Ile | Gly | Gly | Pro | Arg | Ser | Tyr | Thr | Ile |
| Ala | Val | Ala | Ser | Leu | Gly | Lys | Gly | Val | Ala | Cys | Asn |
| Pro | Ala | Cys | Phe | Ile | Thr | Gln | Leu | Leu | Pro | Val | Lys |
| Arg | Lys | Leu | Gly | Phe | Tyr | Glu | Trp | Thr | Ser | Arg | Leu |
| Arg | Ser | His | Ile | Asn | Pro | Thr | Gly | Thr | Val | Leu | Leu |
| Gln | Leu | Glu | Asn | Thr | Met | Gln | Met | Ser | Leu | Lys | Asp |
| Leu | Leu | | | | | | | | | | |

FIG. 9

ATGGCTACAG GTAAGCGCCC CTAAAATCCC TTTGGGCACA

ATGTGTCCTG AGGGGAGAGG CAGCGACCTG TAGATGGGAC

GGGGGCACTA ACCCTCAGGT TTGGGGCTTC TGAATGTGAG

TATCGCCATG TAAGCCCAGT ATTTGGCCAA TCTCAGAAAG

CTCCTGGTCC CTGGAGGGAT GGAGAGAGAA AAACAAACAG

CTCCTGGAGC AGGGAGAGTG CTGGCCTCTT GCTCTCCGGC

TCCCTCTGTT GCCCTCTGGT TTCTCCCCAG GCTCCCGGAC

GTCCCTGCTC CTGGCTTTTG GCCTGCTCTG CCTGCCCTGG

CTTCAAGAGG GCAGTGCC

FIG. 10

ATGGCTACAG GCTCCCGGAC GTCCCTGCTC CTGGCTTTTG

GCCTGCTCTG CCTGCCCTGG CTTCAAGAGG GCAGTGCC

FIG. 11

Met Ala Thr Gly Ser Arg Thr Ser Leu Leu Leu Ala
Phe Gly Leu Leu Cys Leu Pro Trp Leu Gln Glu Gly
Ser Ala

FIG. 12

```
   1 CTGGACAATG GATTGGCAAG GACGCCTACC ATGGGCTGGC TGCACTGGGA GCGCTTCATG
  61 TGCAACCTTG ACTGCCAGGA AGAGCCAGAT TCCTGCATCA GTGAGAAGCT CTTCATGGAG
 121 ATGGCAGAGC TCATGGTCTC AGAAGGCTGG AAGGATGCAG GTTATGAGTA CCCTCTGCATT
 181 GATGACTGTT GGATGGCTCC CCAAAGAGAT TCAGAAGGCA GACTTCAGGC AGACCCTCAG
 241 CGCTTCCTC ATGGGATTCG CCAGCTAGCT AATTATGTTC ACAGCAAAGG ACTGAAGCTA
 301 GGGATTTATG CAGATGTTGG AAATAAAACC TGCGCAGGCT TCCCTGGGAG TTTTGGATAC
 361 TACGACATTG ATGCCCAGAC CTTTGCTGAC TGGGGAGTAG ATCTGCTAAA ATTTGATGGT
 421 TGTTACTGTG ACAGTTTGGA AAATTTGGCA GATGGTTATA AGCACATGTC CTTGGCCCTG
 481 AATAGGACTG GCAGAAGCAT TGTGTACTCC TGTGAGTGGC CTCTTTATAT GTGGCCCTTT
 541 CAAAAGCCCA ATTATACAGA AATCCGACAG TACTGCAATC ACTGGCGAAA TTTTGCTGAC
 601 ATTGATGATT CCTGGAAAAG TATAAAGAGT ATCTTGGACT GGACATCTTT TAACCAGGAG
 661 AGAATTGTTG ATGTTGCTGG ACCAGGGGGT TGGAATGACC CAGATATGTT AGTGATTGGC
 721 AACTTTGGCC TCAGCTGGAA TCAGCAAGTA ACTCAGATGG CCCTCTGGGC TATCATGGCT
 781 GCTCCTTTAT TCATGTCTAA TGACCTCCGA CACATCAGCC CTCAAGCCAA AGCTCTCCTT
 841 CAGGATAAGG ACGTAATTGC CATCAATCAG GACCCCCTTG GCAAGCAAGG GTACCAGCTT
 901 AGACAGGGAG ACAACTTTGA AGTGTGGGAA CGACCTCTCT CAGGCTTAGC CTGGCTGTA
 961 GCTATGATAA ACCGGCAGGA GATTGGTGGA CCTCGCTCTT ATACCATCGC AGTTGCTTCC
1021 CTGGGTAAAG GAGTGGCCTG TAATCCTGCC TGCTTCATCA CACAGCTCCT CCCTGTGAAA
1081 AGGAAGCTAG GGTTCTATGA ATGGACTTCA AGGTTAAGAA GTCACATAAA TCCCACAGGC
1141 ACTGTTTTGC TTCAGCTAGA AAATACAATG CAGATGTCAT TAAAAGACTT ACTTTAA
```

FIG. 13

TRANFECTED HUMAN CELLS EXPRESSING HUMAN α-GALACTOSIDASE A PROTEIN

CROSS REFERENCE TO RELATED APPLICATIONS

This application claims the benefit of U.S. provisional application Ser. No. 60/026,041, filed on Sep. 13, 1996.

BACKGROUND OF THE INVENTION

This invention relates to α-galactosidase A and treatment for α-galactosidase A deficiency.

Fabry disease is an X-linked inherited lysosomal storage disease characterized by symptoms such as severe renal impairment, angiokeratomas, and cardiovascular abnormalities, including ventricular enlargement and mitral valve insufficiency. The disease also affects the peripheral nervous system, causing episodes of agonizing, burning pain in the extremities. Fabry disease is caused by a deficiency in the enzyme α-galactosidase A (α-gal A), which results in a blockage of the catabolism of neutral glycosphingolipids, and accumulation of the enzyme's substrate, ceramide trihexoside, within cells and in the bloodstream.

Due to the X-linked inheritance pattern of the disease, essentially all Fabry disease patients are male. Although a few severely affected female heterozygotes have been observed, female heterozygotes are generally either asymptomatic or have relatively mild symptoms largely limited to a characteristic opacity of the cornea. An atypical variant of Fabry disease, exhibiting low residual α-gal A activity and either very mild symptoms or apparently no other symptoms characteristic of Fabry disease, correlates with left ventricular hypertrophy and cardiac disease (Nakano et al., New Engl. J. Med. 333:288–293, 1995). It has been speculated that reduction in α-gal A may be the cause of such cardiac abnormalities.

The cDNA and gene encoding human α-gal A have been isolated and sequenced (Bishop et al., Proc. Natl. Acad. Sci. USA 83:4859, 1986; Kornreich et al., Nuc. Acids Res. 17:3301, 1988; Oeltjen et al., Mammalian Genome 6:335–338, 1995). Human α-gal A is expressed as a 429-amino acid polypeptide, of which the N-terminal 31 amino acids constitute a signal peptide. The human enzyme has been expressed in Chinese Hamster Ovary (CHO) cells (Desnick, U.S. Pat. No. 5,356,804; Ioannou et al., J. Cell Biol. 119:1137, 1992); insect cells (Calhoun et al., U.S. Pat. No. 5,179,023); and COS cells (Tsuji et al., Eur. J. Biochem. 165:275, 1987). Pilot trials of α-gal A replacement therapies have been reported, using protein derived from human tissues (Mapes et al., Science 169:987 1970; Brady et al., N. Engl. J. Med. 289:9, 1973; Desnick et al., Proc. Natl. Acad. Sci. USA 76:5326, 1979), but there is currently no effective treatment for Fabry disease.

SUMMARY OF THE INVENTION

It has been found that expressing a DNA encoding human α-gal A in cultured human cells produces a polypeptide that is glycosylated appropriately, so that it is not only enzymatically active and capable of acting on the glycosphingolipid substrate which accumulates in Fabry disease, but is also efficiently internalized by cells via cell surface receptors which target it exactly to where it is needed in this disease: the lysosomal compartment of affected cells, particularly the endothelial cells lining the patient's blood vessels. This discovery, which is discussed in more detail below, means that an individual suspected of having an α-gal A deficiency such as Fabry disease can be treated either with (1) human cells that have been genetically modified to overexpress and secrete human α-gal A, or (2) purified human α-gal A obtained from cultured, genetically modified human cells.

Therapy via the first route, i.e., with the modified cells themselves, involves genetic manipulation of human cells (e.g., primary cells, secondary cells, or immortalized cells) in vitro or ex vivo to induce them to express and secrete high levels of human α-gal A, followed by implantation of the cells into the patient, as generally described in Selden et al., WO 93/09222 (herein incorporated by reference).

When cells are to be genetically modified for the purposes of treatment of Fabry disease by either gene therapy or enzyme replacement therapy, a DNA molecule that contains an α-gal A cDNA or genomic DNA sequence may be contained within an expression construct and introduced into primary or secondary human cells (e.g., fibroblasts, epithelial cells including mammary and intestinal epithelial cells, endothelial cells, formed elements of the blood including lymphocytes and bone marrow cells, glial cells, hepatocytes, keratinocytes, muscle cells, neural cells, or the precursors of these cell types) by standard methods of transfection including, but not limited to, liposome-, polybrene-, or DEAE dextran-mediated transfection, electroporation, calcium phosphate precipitation, microinjection, or velocity driven microprojectiles ("biolistics"). Alternatively, one could use a system that delivers DNA by viral vector. Viruses known to be useful for gene transfer include adenoviruses, adeno associated virus, herpes virus, mumps virus, poliovirus, retroviruses, Sindbis virus, and vaccinia virus such as canary pox virus. Although primary or secondary cell cultures are preferred for the therapy methods of the invention, one can also use immortalized human cells. Examples of immortalized human cell lines useful in the present methods include, but are not limited to, Bowes Melanoma cells (ATCC Accession No. CRL 9607), Daudi cells (ATCC Accession No. CCL 213), HeLa cells and derivatives of HeLa cells (ATCC Accession Nos. CCL 2, CCL 2.1, and CCL 2.2), HL-60 cells (ATCC Accession No. CCL 240), HT1080 cells (ATCC Accession No. CCL 121), Jurkat cells (ATCC Accession No. TIB 152), KB carcinoma cells (ATCC Accession No. CCL 17), K-562 leukemia cells (ATCC Accession No. CCL 243), MCF-7 breast cancer cells (ATCC Accession No. BTH 22), MOLT-4 cells (ATCC Accession No. 1582), Namalwa cells (ATCC Accession No. CRL 1432), Raji cells (ATCC Accession No. CCL 86), RPMI 8226 cells (ATCC Accession No. CCL 155), U-937 cells (ATCC Accession No. CRL 1593), WI-38VA13 subline 2R4 cells (ATCC Accession No. CLL 75.1), and 2780AD ovarian carcinoma cells (Van der Blick et al., Cancer Res. 48:5927–5932, 1988) as well as heterohybridoma cells produced by fusion of human cells and cells of another species. Secondary human fibroblast strains, such as WI-38 (ATCC Accession No. CCL 75) and MRC-5 (ATCC Accession No. CCL 171), may also be used.

Following the genetic engineering of human cells with a DNA molecule encoding α-gal A (or following another appropriate genetic modification, as described below) to produce a cell which overexpresses and secretes α-gal A, a clonal cell strain consisting essentially of a plurality of genetically identical cultured primary human cells, or, where the cells are immortalized, a clonal cell line consisting essentially of a plurality of genetically identical immortalized human cells, may be generated. Preferably, the cells of the clonal cell strain or clonal cell line are fibroblasts.

The genetically modified cells can then be prepared and introduced into the patient by appropriate methods, e.g. as described in Selden et al., WO 93/09222.

Gene therapy in accordance with the invention possesses a number of advantages over enzyme replacement therapy with enzyme derived from human or animal tissues. For example, the method of the invention does not depend upon the possibly inconsistent availability of sources of appropriate tissues, and so is a commercially viable means of treating α-gal A deficiency. It is relatively risk-free compared to enzyme-replacement therapy with enzyme derived from human tissues, which may be infected with known or unknown viruses and other infective agents. Furthermore, gene therapy in accordance with the invention possesses a number of advantages over enzyme replacement therapy in general. For example, the method of the invention (1) provides the benefits of a long-term treatment strategy that eliminates the need for daily injections; (2) eliminates the extreme fluctuations in serum and tissue concentrations of the therapeutic protein, which typically accompany conventional pharmacologic delivery; and (3) is likely to be less expensive than enzyme replacement therapy because production and purification of the protein for frequent administration are unnecessary.

As described above, individuals with α-gal A deficiencies may also be treated with purified α-gal A (i.e. enzyme replacement therapy). Primary, secondary, or immortalized human cells genetically modified to overexpress human α-gal A will also be useful for in vitro protein production, to produce protein which may be purified for enzyme replacement therapy. Secondary or immortalized human cells may be chosen from among those described above and may be genetically modified by the transfection or transduction methods also described above. After genetic modification, the cells are cultured under conditions permitting overexpression and secretion of α-gal A. The protein is isolated from the cultured cells by collecting the medium in which the cells are grown, and/or lysing the cells to release their contents, and then applying standard protein purification techniques. One such technique involves passing the culture medium, or any sample containing human α-gal A, over a hydrophobic interaction resin such as Butyl Sepharose® or another resin having a functional moiety that includes a butyl group. Passing the sample over such a resin may constitute the first chromatography step. If further purification is required, the α-gal A-containing material eluted from the hydrophobic interaction resin may be passed over a column containing a second resin, such as an immobilized heparin resin such as Heparin Sepharose®, hydroxyapatite, an anion exchange resin such as Q Sepharose®, or a size exclusion resin such as Superdex® 200. Preferably, the purification protocol would include use of each of the above types of resins. Alternatively, one could use one or more of the latter resins before or instead of the hydrophobic interaction resin.

Previous methods for the preparation of α-gal A with relatively high purity were dependent on the use of affinity chromatography, using a combination of lectin affinity chromatography (concanavalin A (Con A) Sepharose) and affinity chromatography based on binding of α-gal A to the substrate analog N-6-aminohexanoyl-α-D-galactosylamine coupled to a Sepharose matrix (Bishop et al., J. Biol. Chem. 256:1307–1316, 1981). The use of proteinaceous lectin affinity resins and substrate analog resins is typically associated with the continuous leaching of the affinity agent from the solid support (cf. Marikar et al., Anal. Biochem. 201:306–310, 1992), resulting in contamination of the purified product with the affinity agent either free in solution or bound to eluted protein. Such contaminants make the product unsuitable for use in pharmaceutical preparations. Bound substrate analogs and lectins can also have substantial negative effects on the enzymatic, functional, and structural properties of proteins. Furthermore, such affinity resins are typically expensive to prepare, making the use of such resins less suitable for production on a commercial scale than more conventional chromatography resins. Thus, the development of a purification protocol using conventional chromatography resins, which are readily available in supplies and quality suitable for large-scale commercial use, is a significant advantage of the present invention.

An individual who is suspected of having an α-gal A deficiency may be treated by administration of pharmaceutically acceptable, purified human α-gal A by any standard method, including but not limited to intravenous, subcutaneous, or intramuscular injection, or as a solid implant. The purified protein may be formulated in a therapeutic composition consisting of an aqueous solution containing a physiologically acceptable excipient, e.g. a carrier such as human serum albumin, at pH 6.5 or below.

The present invention thus provides a means for obtaining large quantities of appropriately glycosylated and therefore therapeutically useful human α-gal A. This makes enzyme replacement therapy for α-gal deficiency commercially viable, as well as relatively risk-free compared to therapy with enzyme derived from human or animal tissues.

Skilled artisans will recognize that the human α-gal A DNA sequence (either cDNA or genomic DNA), or sequences that differ from it due to either silent codon changes or to codon changes that produce conservative amino acid substitutions, can be used to genetically modify cultured human cells so that they will overexpress and secrete the enzyme. It is also possible that certain mutations in the α-gal A DNA sequence will encode polypeptides that retain or exhibit improved α-gal A enzymatic activity (as would be apparent by expressing the mutant DNA molecule in cultured cells, purifying the encoded polypeptide, and measuring the catalytic activity, as described herein). For example, one would expect conservative amino acid substitutions to have little or no effect on the biological activity, particularly if they represent less than 10% of the total number of residues in the protein. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

Production of α-gal A by the cells can be maximized by certain genetic manipulations. For example, the DNA molecule that encodes α-gal A may also encode an heterologous signal peptide, such as the signal peptide of human growth hormone (hGH), erythropoietin, Factor VIII, Factor IX, glucagon, the low density lipoprotein (LDL) receptor, or a lysosomal enzyme other than α-gal A. Preferably, the signal peptide is the hGH signal peptide (SEQ ID NO:21), and is at the N-terminus of the encoded protein. The DNA sequence encoding the signal peptide may contain an intron such as the first intron of the hGH gene, resulting in a DNA sequence such as SEQ ID NO:27 (see also FIG. 10). Furthermore, the DNA molecule may also contain a 3' untranslated sequence (UTS) that is at least 6 nucleotides in length (in contrast to the α-gal A mRNA found in humans, which has no 3' UTS, the requisite polyadenylation site being within the coding sequence). The UTS is positioned immediately 3' to the termination codon of the coding sequence, and includes a polyadenylation site. It is preferably at least 6 nucleotides in length, more preferably at least 12, and most preferably at least 30, and in all cases it contains the sequence AATAAA or a related sequence which serves to promote polyadenylation. A DNA molecule as described, i.e., encoding an hGH signal peptide linked to α-gal A and containing a 3' UTS that includes a polyadenylation site, and preferably including expression control sequences, is also within the invention. Also within the scope of the invention is a DNA molecule encoding a protein that includes the signal peptide of hGH linked to α-gal A or any other heterologous polypeptide (i.e., any polypeptide other than hGH or an analog of hGH). The heterologous polypeptide is typically a mammalian protein, e.g. any medically desirable human polypeptide.

Other features and advantages of the invention will be apparent from the detailed description that follows, and from the claims.

The term "genetically modified," as used herein in reference to cells, is meant to encompass cells that express a particular gene product following introduction of a DNA molecule encoding the gene product and/or regulatory elements that control expression of a coding sequence. The introduction of the DNA molecule may be accomplished by gene targeting (i.e., introduction of a DNA molecule to a particular genomic site); furthermore homologous recombination allows replacement of the defective gene itself (the defective α-gal A gene or a portion of it could be replaced in a Fabry disease patient's own cells with the whole gene or a portion thereof)).

The term "α-gal A," as used herein, means α-gal A without a signal peptide, i.e., SEQ ID NO:26 (FIG. 9). There is some indication that residues 371 to 398 or 373 to 398 of SEQ ID NO:26 (FIG. 9) may be removed in the lysosome; however, removal of this putative propeptide is not believed to affect activity of the enzyme. This suggests that any portion of the putative propeptide could be deleted without affecting activity. Thus, the term "α-gal A" as used herein also covers a protein having a sequence corresponding to SEQ ID NO:26 except lacking up to 28 residues at the C-terminus of that sequence. By "α-gal A deficiency" is meant any deficiency in the amount or activity of this enzyme in a patient. The deficiency may induce severe symptoms as typically observed in males who are suffering from Fabry disease, or may be only partial and induce relatively mild symptoms as can be seen in heterozygous female carriers of the defective gene.

As used herein, the term "primary cell" includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells.

"Secondary cells" refers to cells at all subsequent steps in culturing. That is, the first time a plated primary cell is removed from the culture substrate and replated (passaged), it is referred to as a secondary cell, as are all cells in subsequent passages.

A "cell strain" consists of secondary cells which have been passaged one or more times; exhibit a finite number of mean population doublings in culture; exhibit the properties of contact-inhibited, anchorage dependent growth (except for cells propagated in suspension culture); and are not immortalized.

By "immortalized cell" is meant a cell from an established cell line that exhibits an apparently unlimited lifespan in culture.

By "signal peptide" is meant a peptide sequence that directs a newly synthesized polypeptide to which it is attached to the endoplasmic reticulum for further post-translational processing and/or distribution.

The term "heterologous signal peptide," as used herein in the context of α-gal A, means a signal peptide that is not the human α-gal A signal peptide (i.e., that encoded by nucleotides 36–128 of SEQ ID NO:18). It typically is the signal peptide of some mammalian protein other than α-gal A.

The term "first chromatography step" refers to the first application of a sample to a chromatography column (all steps associated with the preparation of the sample are excluded).

BRIEF DESCRIPTION OF THE DRAWINGS

FIG. 1 is a representation of the 210 bp probe that was used to isolate α-gal A from a human fibroblast cDNA library (SEQ ID NO:19). The sequence is from exon 7 of the α-gal A gene. The probe was isolated from human genomic DNA by the polymerase chain reaction (PCR). The regions underlined in the figure correspond to the sequences of the amplification primers.

FIG. 2 is a representation of the sequence of the DNA fragment that completes the 5' end of the α-gal A cDNA clone (SEQ ID NO:20). This fragment was amplified from human genomic DNA by PCR. The regions underlined correspond to the sequences of the amplification primers. The positions of the NcoI and SacII restriction endonuclease sites, which were used for subcloning as described in Example IA, are also shown.

FIG. 3 is a representation of the sequence of α-gal A cDNA, including the sequence that encodes the signal peptide (SEQ ID NO:18).

FIG. 9 is a representation of the human α-gal A amino acid sequence (SEQ ID NO:26).

FIG. 10 is a representation of the DNA sequence encoding the hGH signal peptide and containing the first hGH intron (underlined) (SEQ ID NO:27).

FIG. 11 is a representation of the DNA sequence encoding the hGH signal peptide without the intron (SEQ ID NO:22).

FIG. 12 is a representation of the amino acid sequence of the hGH signal peptide (SEQ ID NO:21).

FIG. 13 is a representation of the cDNA sequence encoding human α-gal A (without signal peptide) (SEQ ID NO:25).

DETAILED DESCRIPTION

Figure 4:
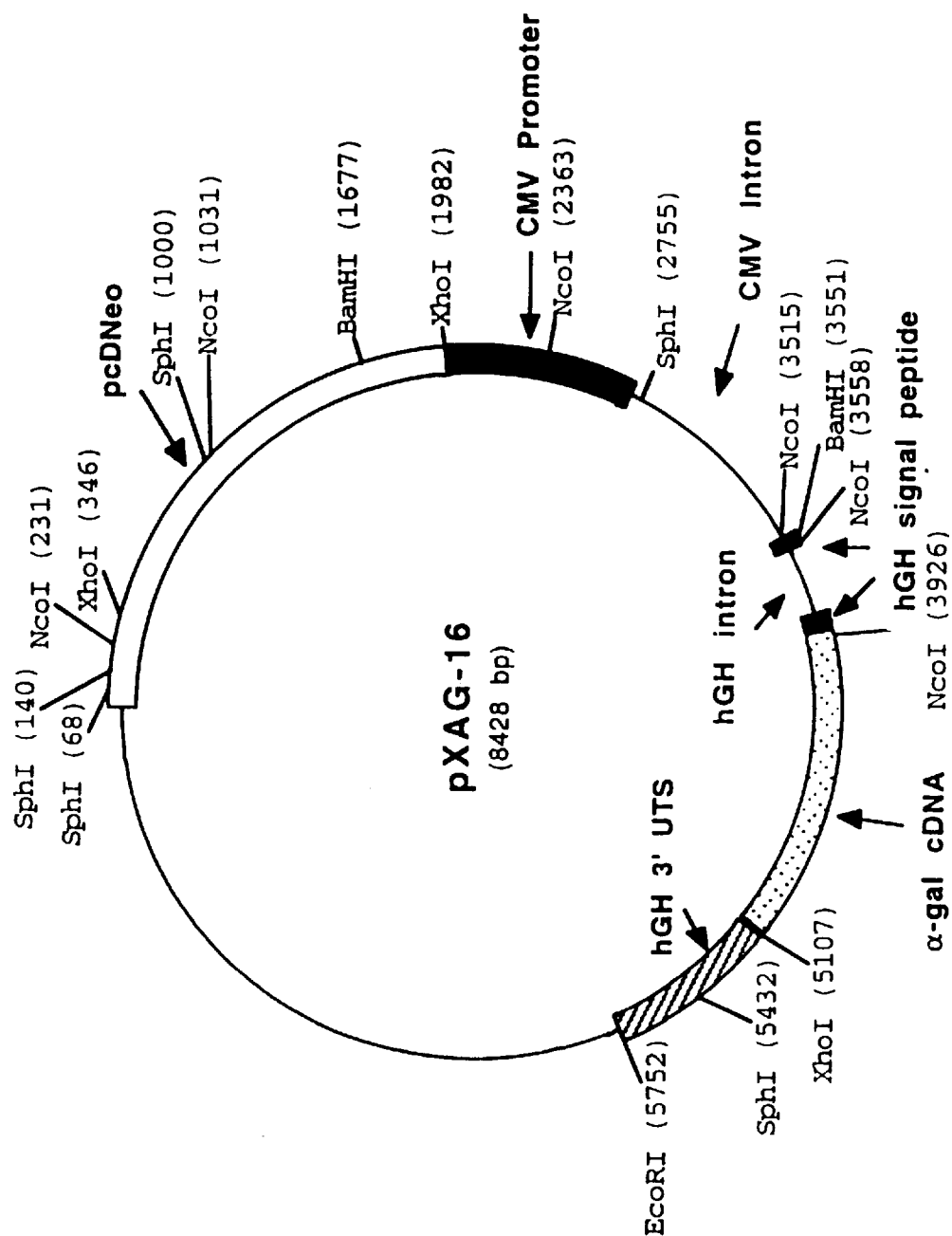
FIG. 4 is a schematic map of pXAG-16, an α-gal A expression construct that includes the CMV (cytomegalovirus) promoter and intron, the hGH signal peptide coding sequence and first intron, the cDNA for α-gal A (i.e., lacking the α-gal A signal peptide sequence) and the hGH 3' UTS.

Lysosomal enzymes such as α-gal A are targeted to the lysosomal compartment of a cell through interaction with the mannose-6-phosphate (M6P) receptor, which binds to M6P residues present in the oligosaccharide moieties of enzymes destined for the lysosomal compartment (Kornfeld, S. and Mellman, I, Ann. Rev. Cell Biol. 5:483–525, 1989). The primary interaction occurs in the Golgi, where enzymes bound to Golgi M6P receptors are segregated for transport to the lysosomes. A secondary type of interaction is believed to take place between extracellular α-gal A and M6P receptors at the cell surface. Extracellular substances internalized by cells are transported through the cytoplasm in endocytic vesicles, which fuse with primary lysosomes and empty their contents into the lysosomes. In this process, cell surface M6P receptors are also incorporated into endocytic vesicles and transported to lysosomes.

Any α-gal A present in the extracellular milieu can, if it bears M6P residues, bind to the cell surface M6P receptors and thereby be transported into the lysosomal compartment along with the receptors. Once in the lysosomal compartment as a result of this scavenger pathway, the enzyme can carry out its appropriate function. Thus, even if a cell is genetically deficient in producing its own α-gal A, there exists a mechanism for it to take up exogenously produced enzyme, provided that (a) the enzyme is suitably glycosylated and (b) the deficient cell bears M6P receptors.

In Fabry disease, vascular endothelial cells of the kidney and heart have been shown to display severe histopathologic abnormalities and contribute to the clinical pathology of the disease; these cells, which do carry M6P receptors, are a particular target of the presently claimed invention. The α-gal A produced in accordance with the invention may be delivered either locally or systemically to the affected cells, by gene therapy (i.e., by genetically modified cells which express and secrete the glycosylated enzyme within the patient), or by conventional pharmacologic routes of administration. An α-gal A in which M6P is present in the N-linked oligosaccharides is therefore of great importance for therapy in accordance with the invention.

Furthermore, the degree to which the N-linked oligosaccharides of α-gal A are modified by sialylation is also of great importance. In the absence of appropriate sialylation, α-gal A will be rapidly cleared from the circulation due to binding by hepatic asialoglycoprotein receptors, followed by internalization and degradation by hepatocytes (Ashwell and Harford, Ann. Rev. Biochem. 51:531–554, 1982). This decreases the amount of α-gal A available in the circulation for binding to M6P receptors on cells which contribute to the clinical pathology of Fabry disease, such as the vascular endothelial cells of the kidney and heart. Surprisingly, the Applicants have found that α-gal A secreted by stably transfected human cells has glycosylation properties which are suitable for the treatment of Fabry disease by either gene therapy or by conventional pharmaceutical administration of the purified secreted protein. This is in contrast to the situation with the best-studied lysosomal enzyme, glucocerebrosidase, in which delivery of the enzyme purified from human placenta or secreted from transfected CHO cells to the clinically-relevant cells in the body requires complex enzymatic modification of the enzyme following purification (cf. Beutler, New Engl. J. Med. 325:1354–1360, 1991).

The therapy of the invention can be carried out in either of two general ways: by introducing into the patient a therapeutically effective amount of purified human α-gal A obtained from cultured human cells genetically modified to overexpress and secrete the enzyme, or by introducing the overexpressing cell itself into the patient. Techniques to accomplish the necessary genetic modifications are discussed below, as are the methods of purification, formulation, and treatment.

EXAMPLE I

Preparation and Use of Constructs Designed to Deliver and Express α-Gal A

Two expression plasmids, pXAG-16 and pXAG-28, were constructed. These plasmids contain human α-gal A cDNA encoding the 398 amino acids of the α-gal A enzyme (without the α-gal A signal peptide); the human growth hormone (hGH) signal peptide genomic DNA sequence, which is interrupted by the first intron of the hGH gene; and the 3' untranslated sequence (UTS) of the hGH gene, which contains a signal for polyadenylation. Plasmid pXAG-16 has the human cytomegalovirus immediate-early (CMV IE) promoter and first intron (flanked by non-coding exon sequences), while pXAG-28 is driven by the collagen Iα2 promoter and also contains the β-actin gene's 5' UTS, which contains the first intron of the β-actin gene.

A. Cloning of the Complete α-Gal A cDNA, and Construction of the α-Gal A Expression Plasmid pXAG-16

The human α-gal cDNA was cloned from a human fibroblast cDNA library that was constructed as follows. Poly-A$^+$ mRNA was isolated from total RNA, and cDNA synthesis was performed using reagents for the lambda ZapII® system according to the manufacturer's instructions (Stratagene Inc., LaJolla, Calif.). Briefly, "first strand" cDNA was generated by reverse transcription in the presence of an oligo-dT primer containing an internal XhoI restriction endonuclease site. Following treatment with RNase H, the cDNA was nick-translated with DNA polymerase I to generate double stranded cDNA. This cDNA was made blunt-ended with T4 DNA polymerase, and ligated to EcoRI adaptors.

The products of this ligation were treated with T4 DNA kinase and digested with XhoI. The cDNA was fractionated by Sephacryl-400® chromatography. Large and medium size fractions were pooled and the cDNAs ligated to EcoRI and XhoI-digested Lambda ZapII arms. The products of this ligation were then packaged and titered. The primary library had a titer of $1.2 \times 10^7$ pfu/ml and an average insert size of 925 bp.

A 210 bp probe from exon 7 of the human α-gal A gene (FIG. 1, SEQ ID NO:19) was used to isolate the cDNA. The probe itself was isolated from genomic DNA by the polymerase chain reaction (PCR) using the following oligonucleotides: 5'-CTGGGCTGTAGCTATGATAAAC-3' (Oligo 1; SEQ ID NO:1) and 5'-TCTAGCTGAAGCAAAACAGTG-3' (Oligo 2; SEQ ID NO:2). The PCR product was then used to screen the fibroblast cDNA library, and positive clones were isolated and further characterized. One positive clone, phage 3A, was subjected to the lambda ZapII® system excision protocol (Stratagene, Inc., La Jolla, Calif.), according to the manufacturer's instructions. This procedure yielded plasmid pBSAG3A, which contains the α-gal A cDNA sequence in the pBluescriptSK™ plasmid backbone. DNA sequencing revealed that this plasmid did not contain the complete 5' end of the cDNA sequence. Therefore, the 5' end was reconstructed using a PCR fragment amplified from human genomic DNA. To accomplish this, a 268 bp genomic DNA fragment (FIG. 2, SEQ ID NO:20) was amplified using the following oligonucleotides:

5'-ATTGGTCCGCCCCTGAGGT-3' (Oligo 3; SEQ ID NO:3) and 5'-TGATGCAGGAATCTGGCTCT-3' (Oligo 4; SEQ ID NO:4). This fragment was subcloned into a "TA" cloning plasmid (Invitrogen Corp., San Diego, Calif.) to generate plasmid pTAAGEI. Plasmid pBSAG3A, which contains the majority of the α-gal A cDNA sequence, and pTAAGEI, which contains the 5' end of the α-gal A cDNA, were each digested with SacII and NcoI. The positions of the relevant SacII and NcoI sites within the amplified DNA fragment are shown in FIG. 2. The 0.2 kb SacII-NcoI fragment from pTAAGEI was isolated and ligated to equivalently digested pBSAG3A. This plasmid, pAGAL, contains the complete α-gal A cDNA sequence, including the sequence encoding the α-gal A signal peptide. The cDNA was completely sequenced (shown in FIG. 3 including the α-gal A signal peptide; SEQ ID NO: 18) and found to be identical to the published sequence for the human α-gal A cDNA (Genbank sequence HUMGALA).

The plasmid pXAG-16 was constructed via several intermediates, as follows. First, pAGAL was digested with SacII and XhoI and blunt-ended. Second, the ends of the complete u-gal A cDNA were ligated to XbaI linkers and subcloned into XbaI digested pEF-BOS (Mizushima et al., Nucl. Acids Res. 18:5322, 1990), creating pXAG-1. This construct contains the human granulocyte-colony stimulating factor (G-CSF) 3' UTS and the human elongation factor-1α (EF-1α) promoter flanking the cDNA encoding α-gal A plus the α-gal A signal peptide, such that the 5' end of the α-gal A CDNA is fused to the EF-1α promoter. To create a construct with the CMV IE promoter and first intron, the α-gal A cDNA and G-CSF 3' UTS were removed from pXAG-1 as a two kb XbaI-BamHI fragment. The fragment was blunt-ended, ligated to BamHI linkers, and inserted into BamHI digested pCMVflpNeo (which was constructed as described below). The orientation was such that the 5' end of the α-gal A cDNA was fused to the CMV IE promoter region.

pCMVflpNeo was created as follows. A CMV IE gene promoter fragment was amplified by PCR using CMV genomic DNA as a template and the oligonucleotides:
5'-TTTTGGATCCCTCGAGGACATTGATTATTGACTAG-3' (SEQ ID NO:23) and 5'-TTTTGGATCCCGTGTCAAGGACGGTGAC-3' (SEQ ID NO:24). The resulting product (a 1.6 kb fragment) was digested with BamHI, yielding a CMV promoter-containing fragment with cohesive BamHI-digested ends. The neo expression unit was isolated from plasmid pMClneopA (Stratagene Inc., La Jolla, Calif.) as a 1.1 kb XhoI-BamHI fragment. The CMV promoter-containing and neo fragments were inserted into a BamHI-, XhoI-digested plasmid (pUC12). Notably, pCMVflpNeo contains the CMV IE promoter region, beginning at nucleotide 546 and ending at nucleotide 2105 (of Genbank sequence HS5MIEP), and the neomycin resistance gene driven by the Herpes Simplex Virus (HSV) thymidine kinase promoter (the TKneo gene) immediately 5' to the CMV IE promoter fragment. The direction of transcription of the neo gene is the same as that of the CMV promoter fragment. This intermediate construct was called pXAG-4.

To add the hGH 3' UTS, the GCSF 3' UTS was removed from pXAG-4 as an XbaI-SmaI fragment and the ends of pXAG-4 were made blunt. The hGH 3' UTS was removed from pXGH5 (Selden et al., Mol. Cellular Biol. 6:3173–3179, 1986) as a 0.6 kb SmaI-EcoRI fragment. After blunt-ending this fragment, it was ligated into pXAG-4 immediately after the blunt-ended XbaI site of pXAG-4. This intermediate was called pXAG-7. The TKneo fragment was removed from this plasmid as a HindIII-ClaI fragment and the ends of the plasmid were blunted by "filling-in" with the Klenow fragment of DNA polymerase I. A neomycin resistance gene driven by the SV40 early promoter was ligated in as a blunted ClaI-BsmBI fragment from a digest of pcDNeo (Chen et al., Mol. Cellular Biol. 7:2745–2752, 1987), placing the neo transcription unit in the same orientation as the α-gal A transcription unit. This intermediate was called pXAG-13.

To complete pXAG-16, which has the 26 amino acid hGH signal peptide coding sequence and first intron of the hGH gene, a 2.0 kb EcoRI-BamHI fragment of pXAG-13 was first removed. This fragment included the α-gal A CDNA and the hGH 3' UTS. This large fragment was replaced with 3 fragments. The first fragment consisted of a 0.3 kb PCR product of pXGH5, which contains the hGH signal peptide coding sequence and includes the hGH first intron sequence, from a synthetic BamHI site located just upstream of the Kozak consensus sequence to the end of the hGH signal peptide coding sequence. The following oligonucleotides were used to amplify this fragment (Fragment 1):
5'-TTTTGGATCCACCATGGCTA-3' (Oligo HGH101; SEQ ID NO:5) and 5'-TTTTGCCGGCACTGCCCTCTTGAA-3' (Oligo HGH102; SEQ ID NO:6).

The second fragment consisted of a 0.27 kb PCR product containing sequences corresponding to the start of the cDNA encoding the 398 amino acid α-gal A enzyme (i.e., lacking the α-gal A signal peptide) to the NheI site. The following oligonucleotides were used to amplify this fragment (Fragment 2): 5'-TTTTCAGCTGGACAATGGATTGGC-3' (Oligo AG10; SEQ ID NO:7) and 5'-TTTTGCTAGCTGGCGAATCC-3' (Oligo AG11; SEQ ID NO:8). The third fragment consisted of the NheI-EcoRI fragment of pXAG-7 containing the remaining α-gal A sequence as well as the hGH 3' UTS (Fragment 3).

Fragment 1 (digested with BamHI and NaeI), Fragment 2 (digested with PvuII and NheI), and Fragment 3 were mixed with the 6.5 kb BamHI-EcoRI fragment of pXAG-13 containing the neo gene and the CMV IE promoter and ligated together to generate plasmid pXAG-16 (FIG. 4).

B. Construction of the α-Gal A Expression Plasmid pXAG-28

The human collagen Iα2 promoter was isolated for use in the α-gal A expression construct pXAG-28 as follows. A 408 bp PCR fragment of human genomic DNA containing part of the human collagen Iα2 promoter was isolated using the following oligonucleotides:
5'-TTTTGGATCCGTGTCCCATAGTGTTTCCAA-3' (Oligo 72; SEQ ID NO:9) and 5'-TTTTGGATCCGCAGTCGTGGCCAGTACC-3' (Oligo 73; SEQ ID NO:10).

This fragment was used to screen a human leukocyte library in EMBL3 (Clontech Inc., Palo Alto, Calif.). One positive clone (phage 7H) containing a 3.8 kb EcoRI fragment was isolated and cloned into pBSIISK+ (Stratagene Inc., La Jolla, Calif.) at the EcoRI site (creating pBS/7H.2). An AvrII site was introduced in pBSIISK+ by digesting with SpeI, which cleaves within the pBSIISK+ polylinker, "filling-in" with the Klenow fragment of DNA polymerase I, and inserting the oligonucleotide 5'-CTAGTCCTAGGA-3' (SEQ ID NO:11). This variant of pBSIISK+ was digested with BamHI and AvrII and ligated to the 121 bp BamHI-AvrII fragment of the original 408 bp collagen Iα2 promoter PCR fragment described above, creating pBS/121COL.6.

The plasmid pBS/121COL.6 was digested with XbaI, which cleaves within the pBSIISK+polylinker sequence, "filled-in" with the Klenow fragment of DNA polymerase I, and digested with AvrII. The 3.8 kb BamHI-AvrII fragment of pBS/7H.2 was isolated and the BamHI site made blunt-ended by treatment with Klenow enzyme. The fragment was then digested with AvrII and ligated to the AvrII-digested vector, thus creating the collagen promoter plasmid pBS/121bpCOL7H.18.

Next the collagen promoter was fused to the 5' UTS of the human β-actin gene, which contains the first intron of the human β-actin gene. To isolate this sequence, a 2 kb PCR fragment was isolated from human genomic DNA using the following oligonucleotides: 5'-TTTTGAGCACAGAGCCTCGCCT-3' (Oligo BA1; SEQ ID NO:12) and 5'-TTTTGGATCCGGTGAGCTGCGAGAATAGCC-3' (Oligo BA2; SEQ ID NO:13).

This fragment was digested with BamHI and BsiHKAI to release a 0.8 kb fragment containing the β-actin 5' UTS and intron. A 3.6 kb SalI-SrfI fragment was then isolated from the collagen promoter plasmid pBS/12lbpCOL7H.18 as follows. pBS/121bpCOL7H.18 was partially digested with BamHI (the BamHI site lies at the 5' end of the collagen Iα2 promoter fragment), made blunt-ended by treatment with the Klenow fragment, and ligated to a SalI linker (5'-GGTCGACC-3'), thereby placing a SalI site upsteam of the collagen Iα2 promoter. This plasmid was then digested with SalI and SrfI (the SrfI site lies 110 bp upstream of the collagen Iα2 promoter CAP site), and the 3.6 kb fragment was isolated. The 0.8 and 3.6 kb fragments were combined with SalI—and BamHI—digested pBSIISK- (Stratagene Inc., La Jolla, Calif.), and a fragment composed of the following four oligonucleotides annealed together (forming a fragment with a blunt end and a BsiHKAI end):
5'-GGGCCCCCAGCCCCAGCCCTCCCATTGGTGGA GGCCCTTTTGGAGGCACCCTAGGGC CAGGAAACTTTTGCCGTAT-3' (Oligo COL-1; SEQ ID NO:14),
5'-AAATAGGGCAGATCCGGGCTTTATTATTTTAGCA CCACGGCCGCCGAGAC CGCGTCCGCCCCGCGAGCA-3' (Oligo COL-2; SEQ ID NO:15),
5'-TGCCCTATTTATACGGCAAAAGTTTCCTGGCCC TAGGGTGCCTCCAAAAGGGC CTCCACCAATGG-GAGGGCTGGGGCTGGGGGCC C-3' (Oligo COL-3; SEQ ID NO:16), and
5'-CGCGGGGCGGACGCGGTCTCGGCGGCCGT GGTGCT AAAATAATAAAGCCCGGATC-3' (Oligo COL-4; SEQ ID NO:17). These four oligonucleotides, when annealed, correspond to the region beginning at the SrfI site of the collagen promoter and continuing through the BsiHKAI site of the β-actin promoter. The resulting plasmid was designated pCOL/β-actin.

Figure 5:
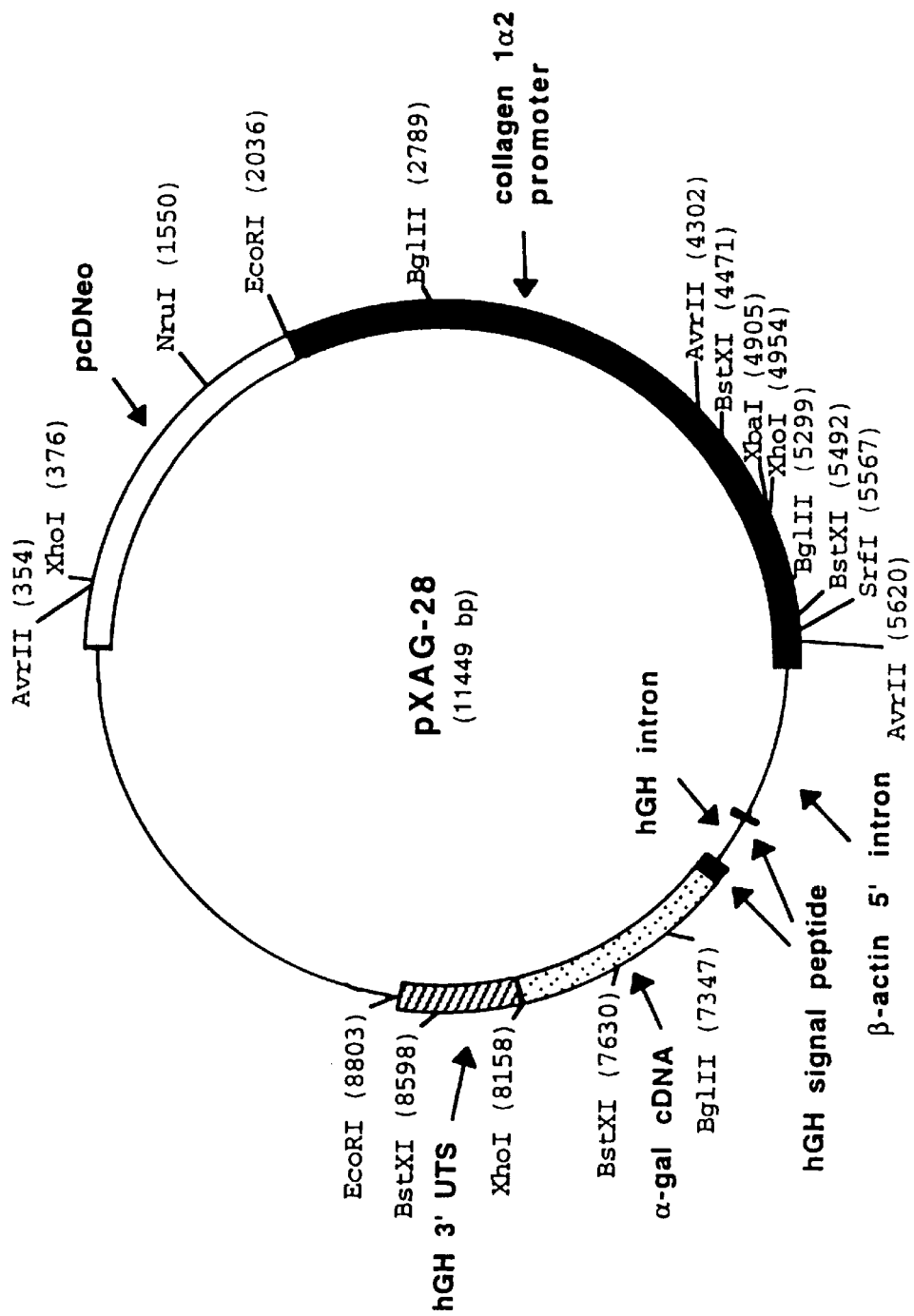
FIG. 5 is a schematic map of pXAG-28, an α-gal A expression construct that includes the collagen Iα2 promoter, a β-actin intron, the hGH signal peptide coding sequence and first intron, the cDNA for α-gal A (i.e., lacking the α-gal A signal peptide sequence) and the hGH 3' UTS.

To complete the construction of pXAG-28, the SalI-BamHI fragment of pCOL/β-actin, containing the collagen Iα2 promoter and β-actin 5' UTS, was isolated. This frag-ment was ligated to two fragments from pXAG-16 (see Example 1A and FIG. 4): (1) the 6.0 kb BamHI fragment (containing the neo gene, plasmid backbone, the CDNA encoding the 398 amino acid α-gal A enzyme, and the hGH 3' UTS); and (2) the 0.3 kb BamHI-XhoI fragment (which contains the SV40 poly A sequence from pcDneo). pXAG-28 contains the human collagen Iα2 promoter fused to the human β-actin 5' UTS, the hGH signal peptide (which is interrupted by the hGH first intron), the cDNA encoding the α-gal A enzyme, and the hGH 3' UTS. A map of the completed expression construct pXAG-28 is shown in FIG. 5.

C. Transfection and Selection of Fibroblasts Electropo-rated with α-Gal A Expression Plasmids In order to express α-gal A in fibroblasts, secondary fibroblasts were cultured and transfected according to published procedures (Selden et al., WO 93/09222).

The plasmids pXAG-13, pXAG-16 and pXAG-28 were transfected by electroporation into human foreskin fibroblasts to generate stably transfected clonal cell strains, and the resulting α-gal A expression levels were monitored as described in Example ID. Secretion of α-gal A by normal foreskin fibroblasts is in the range of 2-10 units/$10^6$ cells/24 hours. In contrast, the transfected fibroblasts displayed mean expression levels as shown in Table 1:

TABLE 1

| Mean α-gal A expression levels (± standard deviation) | |
| --- | --- |
| pXAG-13: | 420 ± 344 U/$10^6$ cells/day |
| | N = 26 clonal strains |
| | (range 3–1133 U/$10^6$ cells/day) |
| pXAG-16: | 2,051 ± 1253 U/$10^6$ cells/day |
| | N = 24 clonal strains |
| | (range 422–5200 U/$10^6$ cells/day) |
| pXAG-28: | 141 ± 131 U/$10^6$ cells/day |
| | N = 38 clonal strains |
| | (range 20–616 U/$10^6$ cells/day) |

These data show that all three expression constructs are capable of increasing α-gal A expression many times that of nontransfected fibroblasts. Expression by fibroblasts stably transfected with pXAG-13, which encodes α-gal A linked to the α-gal A signal peptide, was substantially lower than expression by fibroblasts transfected with pXAG-16, which differs only in that the signal peptide is the hGH signal peptide, the coding sequence of which is interrupted by the first intron of the hGH gene.

Each time the transfected cells were passaged, the secreted α-gal A activity was determined, the cells were counted, and the cell density was calculated. Based on the number of cells harvested and the time allowed for secretion of α-gal A, the specific expression rate of α-gal A was determined and is reported in Tables 2 and 3 as secreted units (of α-gal A) per $10^6$ cells per 24 hour period. Cell strains desirable for gene therapy or for use in generation of material for purification of α-gal A should display stable growth and expression over several passages. Data from the cell strains shown in Tables 2 and 3, which were stably transfected with the α-gal A expression construct pXAG-16, illustrate the fact that α-gal A expression is stably maintained during serial passage.

TABLE 2

Growth and Expression of BRS-11 Cells
Containing the α-Gal A Expression Construct pXAG-16
BRS-11

| Passage | Expression units/$10^6$ cells/24 hr) | Cell Density (cells/cm$^2$) |
|---|---|---|
| 13 | 2601 | $4.80 \times 10^4$ |
| 14 | 1616 | $4.40 \times 10^4$ |
| 15 | 3595 | $4.40 \times 10^4$ |

TABLE 3

Growth and Expression of HF503-242 Cells
Containing the α-Gal A Expression Construct pXAG-16
HF503-242

| Passage | Expression units/$10^6$ cells/24 hr) | Cell Density (cells/cm$^2$) |
|---|---|---|
| 5 | 4069 | $2.80 \times 10^4$ |
| 6 | 7585 | $3.55 \times 10^4$ |
| 7 | 5034 | $2.48 \times 10^4$ |

D. Quantification of α-Gal A Expression

The activity of α-gal A activity was measured using the water-soluble substrate 4-methylumbelliferyl-α-D-galactopyranoside (4-MUF-gal; Research Products, Inc.) by a modification of the protocol described by Ioannou et al. (J. Cell Biol. 119:1137–1150, 1992). The substrate was dissolved in substrate buffer (0.1 M citrate-phosphate, pH 4.6) to a concentration of 1.69 mg/ml (5 mM). Typically, 10 μl of culture supernatant was added to 75 μl of the substrate solution. The tubes were covered and allowed to incubate in a 37° C. waterbath for 60 minutes. At the end of the incubation period, 2 ml of glycine-carbonate buffer (130 mM glycine, 83 mM sodium carbonate, at pH 10.6), were used to stop the reaction. The relative fluorescence of each sample was measured using a model TK0100 fluorometer (Hoefer Scientific Instruments) which has a fixed excitation wavelength of 365 nm and detects a fixed emission wavelength of 460 nm. The readings of the samples were compared to standards prepared from a 1 μM stock of methylumbelliferone (Sigma Chemical Co.), and the amount of hydrolyzed substrate was calculated. The activity of α-gal A is expressed in units; one unit of α-gal A activity is equivalent to one nanomole of substrate hydrolyzed per hour at 37° C. Cell expression data were generally expressed as units of α-gal A activity secreted/$10^6$ cells/24 hours. This assay was also used to measure the amount of α-gal activity in cell lysates and in samples from various α-gal purification steps, as discussed below.

EXAMPLE II

Purification of α-Gal A from the Conditioned Medium of Stably Transfected Human Cell Strains Examples IIA–IIE illustrate that α-gal A may be purified to near-homogeneity from the conditioned medium of cultured human cell strains that have been stably transfected to produce the enzyme.

Figure 6:
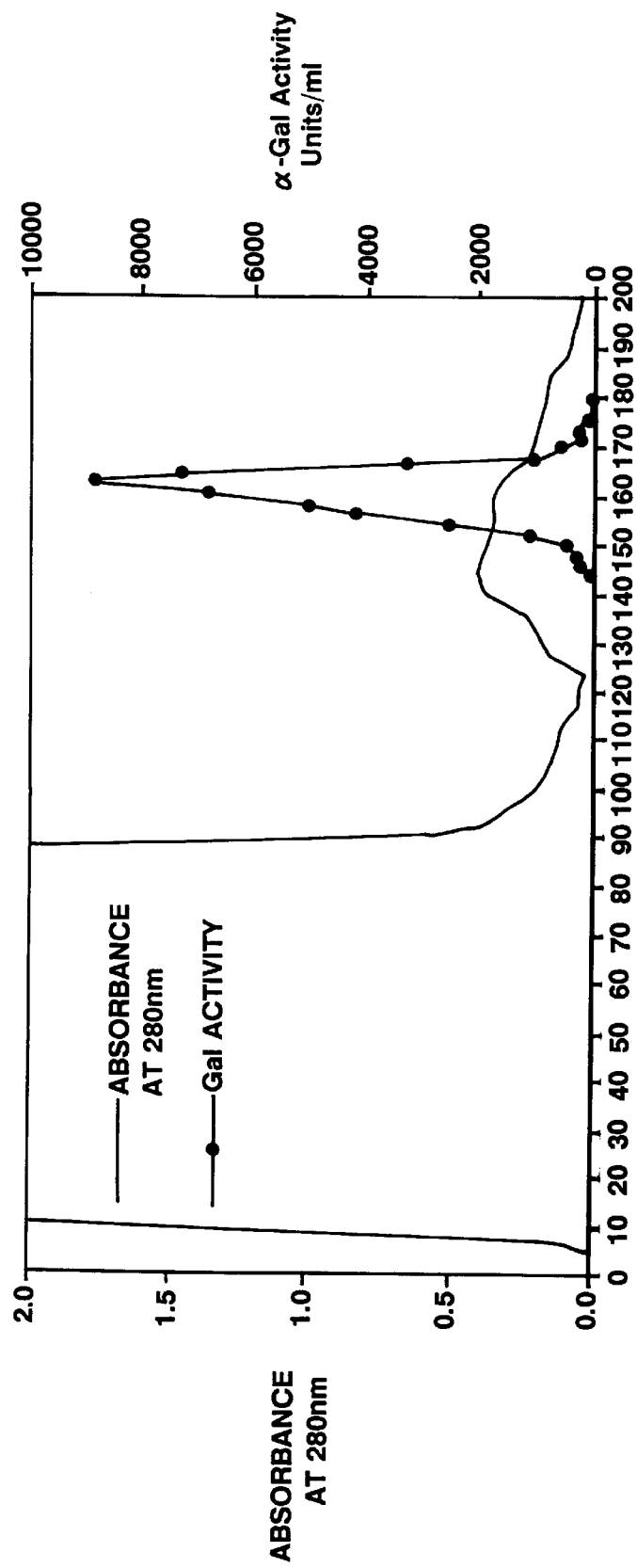
FIG. 6 is a chromatogram of the α-gal A purification step using Butyl Sepharose® resin. The absorbance at 280 nm (plain line) and α-gal A activity (dotted line) of selected fractions is shown.

A. Use of Butyl Sepharose® Chromatography as a First Step in the Purification of α-Gal A Cold conditioned medium (1.34 liters) was clarified by centrifugation and filtered through a 0.45 μm cellulose acetate filter using glass fiber prefilters. While stirring, the pH of the cold, filtered medium was adjusted to 5.6 by the dropwise addition of 1 N HCl, and ammonium sulfate was added to a final concentration of 0.66 M by the dropwise addition of a stock solution (room temperature) of 3.9 M ultrapure ammonium sulfate. The medium was stirred for an additional 5 minutes at 4° C., filtered as before, and applied to a Butyl Sepharose® 4 Fast Flow column (81 ml column volume, 2.5×16.5 cm; Pharmacia, Uppsala, Sweden) that had been equilibrated in 10 mM MES-Tris, pH 5.6, containing 0.66 M ammonium sulfate (buffer A). The chromatography was performed at 4° C. on a Gradi-Frac™ System (Pharmacia, Uppsala, Sweden) equipped with in-line UV (280 nm) and conductivity monitors for assessing total protein and salt concentration, respectively. After sample application at a flow rate of 10 ml/min, the column was washed with 10 column volumes of buffer A. The α-gal A was eluted from the Butyl Sepharose® column with a 14 column volume linear gradient from buffer A (containing ammonium sulfate) to 10 mM MES-Tris, pH 5.6 (no ammonium sulfate). Fractions were assayed for i-gal A activity by the 4-MUF-gal assay, and those containing appreciable enzyme activity were pooled. As seen in FIG. 6 and the purification summary (Table 3), this step removes approximately 99% of the contaminating protein (pre-column sample=8.14 g total protein; post-column sample=0.0638 g total protein).

TABLE 4

Purification of α-Gal A from the Conditioned Medium of Stably Transfected Human Fibroblasts

| Purification Step | Volume (ml) | α-Gal A Activity (× $10^6$ Units) | Total Protein (mg) | Specific Activity (× $10^6$ Units/mg) | Fold Purification (Cumulative) | Percent Recovery |
|---|---|---|---|---|---|---|
| Culture supernatant | 1340 | 14.6 | 8140 | 0.0018 | = 1 | = 100 |
| Butyl Sepharose ® | 417 | 14.1 | 63.8 | 0.221 | 123 | 96.6 |
| Heparin Sepharose ® | 134 | 12.1 | 14.6 | 0.829 | 436 | 82.9 |
| Hydroxyapatite | 47 | 9.73 | 4.46 | 2.18 | 1220 | 66.6 |
| Q Sepharose ® | 31.5 | 8.91 | 3.31 | 2.69 | 1503 | 61.0 |
| Superdex ® 200 | 10 | 8.58 | 2.93 | 2.92 | 1634 | 59.0 |

B. Use of Heparin Sepharose® Chromatography as a Step for Purification of α-Gal A The Butyl Sepharose® column peak fractions were dialyzed at 4° C. against (4 liters) of 10 mM MES-Tris, pH 5.6 (changed once). The conductivity of the dialysate was adjusted to 1.0 mMHO at 4° C. by addition of $H_2O$ or NaCl as necessary. Afterward, the sample was applied to a column of Heparin Sepharose® 6 Fast Flow (Pharmacia, Uppsala, Sweden; 29 ml column volume, 2.5×6 cm) that had been equilibrated in 10 mM MES-Tris, pH 5.6, containing 9 mM NaCl (buffer B). This was done at 4° C. at a flow rate of 10 ml/min. In-line UV (280 nm) and conductivity monitors measured total protein and salt concentration. After the sample was applied, the column was washed with 10 column volumes of buffer B followed by a 3 column volume linear gradient to 8% buffer C/92% buffer B (where buffer C is 10 mM MES-Tris, pH 5.6, containing 250 mM NaCl) and a 10 column volume wash with 8% buffer C. This was followed by elution of α-gal A with a 1.5 column volume linear gradient to 29% buffer C and a subsequent 10 column volume linear gradient to 35% buffer C. Fractions were assayed for α-gal A activity, and those containing appreciable activity were pooled.

C. Use of Hydroxvapatite Chromatography as a Step for Purification of α-Gal A

The heparin pool was filtered and applied directly to a column of Ceramic Hydroxyapatite HC (40 μm; American International Chemical, Natick, Mass.; 12 ml column volume, 1.5×6.8 cm) that had been equilibrated in 1 mM sodium phosphate, pH 6.0 (buffer D). The chromatography was performed at room temperature on a hybrid Gradi-Frac™/FPLC® System (Pharmacia, Uppsala, Sweden) equipped with in-line UV (280 nm) and conductivity monitors. After the sample was applied (5 ml/min), the column was washed with 10 column volumes of buffer D. The α-gal A was eluted with a 7 column volume linear gradient to 42% buffer E/58% buffer D (where buffer E is 250 mM sodium phosphate, pH 6.0) followed by a 10 column volume gradient to 52% buffer E. Fractions were assayed for α-gal A activity, and the fractions containing appreciable activity were pooled.

D. Use of Q Sepharose® Anion Exchange Chromatography as a Step for Purification of α-Gal A The hydroxyapatite pool was diluted approximately 1.5 fold with $H_2O$ to a final conductivity of 3.4–3.6 mMHO at room temperature. After filtering, the sample was applied to a column of Q Sepharose® HP (Pharmacia, Uppsala, Sweden; 5.1 ml column volume, 1.5×2.9 cm) equilibrated in 10% buffer G/90% buffer F, where buffer F is 25 M sodium phosphate, pH 6.0, and buffer G is 25 mM sodium phosphate, pH 6.0, 250 mM NaCl. The chromatography was performed at room temperature on the Gradi-Frac™/FPLC® hybrid system (Pharmacia, Uppsala, Sweden), and total protein and salt concentrations were monitored by the in-line monitors. The sample was applied at a flow rate of 5 ml/min, then the following steps were performed: (1) a 5 column volume wash at 10% buffer G, (2) a 7 column volume wash at 12% buffer G, (3) a 3 column volume linear gradient to 50% buffer G, (4) a 10 column volume linear gradient to 53% buffer G, (5) a 3 column volume gradient to 100% buffer G, and (6) a 10 column volume wash at 100% buffer G. The α-gal A eluted primarily during steps 3 and 4. Fractions containing appreciable activity were pooled (the "Q pool").

E. Use of Superdex®-200 Gel Filtration Chromatography as a Step for Purification of α-Gal A The Q pool was concentrated approximately 5-fold using Centriprep®-10 centrifugal concentrator units (Amicon, Beverly, Mass.), and applied to a column of Superdex® 200 (Pharmacia, Uppsala, Sweden; 189 ml column volume, 1.6×94 cm). The column was equilibrated and eluted with 25 mM sodium phosphate, pH 6.0, containing 150 mM NaCl. The chromatography was performed on an FPLC® system (Pharmacia, Uppsala, Sweden) at room temperature using an in-line UV monitor (280 nm) to follow elution of the protein. The volume of the sample applied to the column was ≦2 ml, the flow rate was 0.5 ml/min, and the fraction size was 2 ml. Multiple column runs were performed; fractions were assayed for α-gal A activity and fractions containing appreciable activity were pooled.

The pooled fractions from the Superdex® 200 column were concentrated using Centriprep-10 units, aliquoted, snap-frozen, and stored at −80° C. for short periods of time. A summary of this example of α-gal A purification is shown in Table 3. The final yield of α-gal A was 59% of the starting material activity, and the specific activity of the purified product was $2.92 \times 10^6$ units/mg protein. The resulting product showed a high level of purity after electrophoresis under reducing conditions on a 4–15% SDS-polyacrylamide gel, which was subsequently silver-stained.

EXAMPLE III

Formulation and Storage of Purified α-Gal A

Highly purified α-gal A is not stable for extended periods of time when stored as a dilute solution of purified protein (≦1 mg protein/ml). Therefore, a formulation was devised to improve stability during prolonged storage, i.e. storage lasting several weeks to at least several months. The purified enzyme was concentrated to at least 1 mg/ml using a centrifugal concentrator (in enzyme buffer consisting of 25 mM sodium phosphate (pH 6.0) and 150 mM NaCl). Human serum albumin (HSA; Buminate®, Baxter-Hyland) was added to a final concentration of 2.5 mg/ml. The protein solution was then sterile filtered using a 0.2 μm cellulose acetate filter (Schleicher and Schuell) attached to a syringe. The α-gal A solution was dispensed into sterile, pyrogen-free glass vials, sealed with a Teflon cap, snap-frozen, and stored at −20° C.

Stability of the α-gal A activity was evaluated over a three month period using the 4-MUF-gal assay. The data presented in Table 5 demonstrate that there was no loss of enzyme activity over the test period. The acidic pH of the formulation (<6.5) is critical to the stability of the highly purified enzyme.

TABLE 5

Stability of Formulated α-Gal A at −20° C.

| Sample | Specific Activity (Units/mg total protein) |
|---|---|
| time 0 | $2.24 \times 10^6 \pm 0.33 \times 10^6$ |
| week 1 | $2.40 \times 10^6 \pm 0.25 \times 10^6$ |
| week 2 | $2.42 \times 10^6 \pm 0.21 \times 10^6$ |
| week 3 | $2.37 \times 10^6 \pm 0.05 \times 10^6$ |
| month 1 | $2.39 \times 10^6 \pm 0.16 \times 10^6$ |
| month 2 | $2.31 \times 10^6 \pm 0.26 \times 10^6$ |
| month 3 | $2.29 \times 10^6 \pm 0.17 \times 10^6$ |

EXAMPLE IV

α-Gal A Produced by Human Cell Strains is Suitable for Treatment of α-Gal A Deficiency The structural and functional properties of purified human α-gal A prepared in accordance with the invention were investigated in order to demonstrate that the DNA molecules described herein and the corresponding expressed glycoproteins produced by transfected human cell strains can be used in gene or enzyme replacement therapies, respectively.

A. Size of α-Gal A Produced by Stably Transfected Human Cells in Culture

The molecular mass of α-gal A was estimated by MALDI-TOF mass spectrometry. These results demonstrate that the molecular mass of the dimer is 102,353 Da, while that of the monomer is 51,002 Da. The expected molecular mass of the monomer, based on amino acid composition, is 45,400 Da. Therefore, it can be inferred that the carbohydrate content of the enzyme accounts for up to 5,600 Da of the molecular weight.

The results of standard amino acid analysis performed on the purified protein are consistent with the conclusion that the protein produced by transfected human cells is identical to the protein purified from human tissues at the amino acid level.

B. N-Terminal Processing of α-Gal A Produced by Stably Transfected Human Cells

The human α-gal A cDNA nucleotide sequence encodes 429 amino acids. The 31 N-terminal amino acids constitute a signal peptide sequence, which is cleaved as the nascent protein transits the endoplasmic reticulum membrane (LeDonne et al., Arch. Biochem. Biophys. 224:186, 1983; Lemansky et al., J. Biol. Chem. 262:2062, 1987). In order to confirm that α-gal A is properly processed when associated with an heterologous signal peptide sequence (for example, the human growth hormone signal sequence) and expressed in transfected human fibroblasts, ten N-terminal amino acids of the secreted protein were microsequenced. Samples were electrophoresed by SDS-PAGE and transferred to ProBlott® (ABI, Foster City, Calif.) using a 10 mM CAPS (pH 11.0), 10% methanol buffer system. The protein on the ProBlott® was visualized by Coomassie staining, and an appropriately sized (50 kDa) band was excised. N-terminal sequence was obtained using an Applied Biosystems pulse-liquid phase amino acid sequenator that performs automated Edman degradation. The N-terminal sequence obtained, LDNGLARTPT (SEQ ID NO:28), is consistent with proper cleavage of the signal peptide and matches the N-terminal sequence predicted for the secreted protein.

C. C-Terminal Amino Acid of α-Gal A Produced by Stably Transfected Human Cells

The C-terminal amino acid residue of secreted α-gal A produced in accordance with the invention was identified using an automated Hewlett Packard C-terminal sequencer. The results indicated a leucine residue at the C-terminus, which agrees with the C-terminal amino acid predicted by the DNA sequence.

D. Carbohydrate Modification of α-Gal A Produced by Stably Transfected Human Cells The glycosylation pattern of α-gal A produced in accordance with the invention was also evaluated. Proper glycosylation is important for optimal in vivo activity of α-gal A; α-gal A expressed in non-glycosylating systems is inactive or unstable (Hantzopolous et al., Gene 57:159, 1987). Glycosylation is also important for the internalization of α-gal A into the desired target cells, and affects the circulating half-life of the enzyme in vivo. On each subunit of i-gal A there are four sites available for addition of asparagine-linked carbohydrate chains, of which only three are occupied (Desnick et al., In *The Metabolic and Molecular Bases of Inherited Disease*, pp 2741–2780, McGraw Hill, New York, 1995).

A sample of α-gal A produced by stably transfected cells was treated with neuraminidase, which is isolated from *A. urafaciens*, (Boehringer-Mannheim, Indianapolis, Ind.) to remove sialic acid. This reaction was performed by treating 5 μg of α-gal A overnight with 10 mU of neuraminidase at room temperature in a total volume of 10 μl of acetate buffered saline (ABS, 20 mM sodium acetate, pH. 5.2, 150 mM NaCl).

Purified α-gal A produced by stably transfected cells was also dephosphorylated using alkaline phosphatase (calf intestinal alkaline phosphatase, Boehringer-Mannheim, Indianapolis, Ind.), by treating 5 μg of α-gal A overnight at room temperature with 15 U of alkaline phosphatase in ABS (pH raised to 7.5 with 1 M Tris).

The samples were analyzed by Western blot with an α-gal A-specific antibody. The antibody used was a rabbit polyclonal anti-peptide antibody, which was produced using a peptide representing amino acids 68–81 of α-gal A as an immunogen. Following transfer of the protein to PVDF (Millipore, Bedford, Mass.), the membrane was probed with a 1:2000 dilution of the anti-serum in 2.5% blotto (non-fat dry milk in 20 mM Tris-HCl$_1$, pH 7.5, 0.05% Tween-20). This was followed by detection with goat anti-rabbit IgG conjugated to horseradish peroxidase (Organon Teknika/Cappel, Durham, N.C.; 1:5000 dilution) and reagents of the ECL chemiluminescence kit (Amersham, Arlington Heights, Ind.).

Treatment of α-gal A with neuraminidase results in a slight shift in molecular mass (approximately 1500–2000 Da or 4–6 sialic acids/monomer), suggesting that there is extensive modification of α-gal A with sialic acid. For reference, the plasma form of α-gal A has 5–6 sialic acid residues per monomer, and the placental form has 0.5–1.0 sialic acid residues per monomer (Bishop et al., J. Biol. Chem. 256:1307, 1981).

Another method used to examine the sialic acid and mannose-6-phosphate modifications of α-gal A was isoelectric focusing (IEF), where the samples are separated on the basis of their isoelectric point (pI) or net charge. Thus, removal of charged residues such as sialic acid or phosphate from α-gal A would be expected to alter the mobility of the protein in the IEF system.

To perform the IEF experiment, samples of α-gal A produced in accordance with the invention were treated with neuraminidase and alkaline phosphatase, mixed 1:1 with 2× Novex sample buffer (with 8 M urea, pH 3.0–7.0), and loaded onto a 6 M urea IEF gel (5.5% polyacrylamide) made using Pharmalyte® (Pharmacia, Uppsala, Sweden; pH 3.0–6.5; Pharmalyte® 4–6.5 and 2.5–5.5, 0.25 ml each per gel). Isoelectric point standards (Bio-Rad) were also included. Following electrophoresis, the gel was transferred to PVDF, and Western blot analysis performed as described above.

The α-gal A produced by stably transfected human fibroblasts consisted of three major isoforms with a pI range of approximately 4.4–4.65. These values are similar to the pIs of the plasma and splenic forms of α-gal A (Bishop et al., J. Biol. Chem. 256:1307, 1981). Neuraminidase treatment of the enzyme increased the pI of all three isoforms, indicating that all were modified to some extent by sialic acid. These data suggest that the α-gal A produced by stably transfected human cells should have a desirable plasma half-life, indicating that this material is well suited for pharmacologic use. Further, treatment of neuraminidase-treated α-gal A with alkaline phosphatase further increased the pI of a portion of the protein to approximately 5.0–5.1, indicating that the enzyme bears one or more mannose-6-phosphate residues. This modification is significant in that it is required for efficient internalization of α-gal A by the target cells.

E. Specific Activity of α-gal A Purified from Stably Transfected Fibroblasts

The potency or specific activity of purified α-gal A is calculated by measuring both the catalytic activity of the enzyme (with the 4-MUF-gal assay), and the protein concentration. The protein concentration can be determined by any standard method, such as with the BCA system (Pierce), or by measuring the absorbance at 280 nm and using the mg/ml extinction coefficient of 2.3 (determined from amino acid analysis) to calculate the value. Using these techniques, the specific activity of α-gal A purified from the conditioned medium of transfected human fibroblasts is 2.2–2.9×10$^6$ units/mg of protein, which is comparable to the specific activity of α-gal A that is purified from human tissues (Bishop et al., J. Biol. Chem. 256:1301, 1981).

F. Mannose or Mannose-6-Phosphate Mediated Internalization of α-Gal A

In order for the α-gal A produced by stably transfected cells to be an effective therapeutic agent for α-gal A deficiencies, the enzyme must be internalized by the affected cells. α-Gal A is not active at physiological pH levels, and is unlikely to be effective in the blood or interstitial fluids. It metabolizes accumulated lipid substrates optimally only when internalized in the acidic environment of the lysosome. This internalization is mediated by the binding of α-gal A to mannose-6-phosphate (M6P) receptors, which are expressed on the cell surface and deliver the enzyme to the lysosome via the endocytic pathway. The M6P receptor is ubiquitously expressed; most somatic cells express it to some extent. The mannose receptor, which is specific for exposed mannose residues on glycoproteins, is less prevalent. The latter receptors are generally found only on macrophage and macrophage-like cells, and provide an additional means of α-gal A entry into these cell types.

Figure 7:
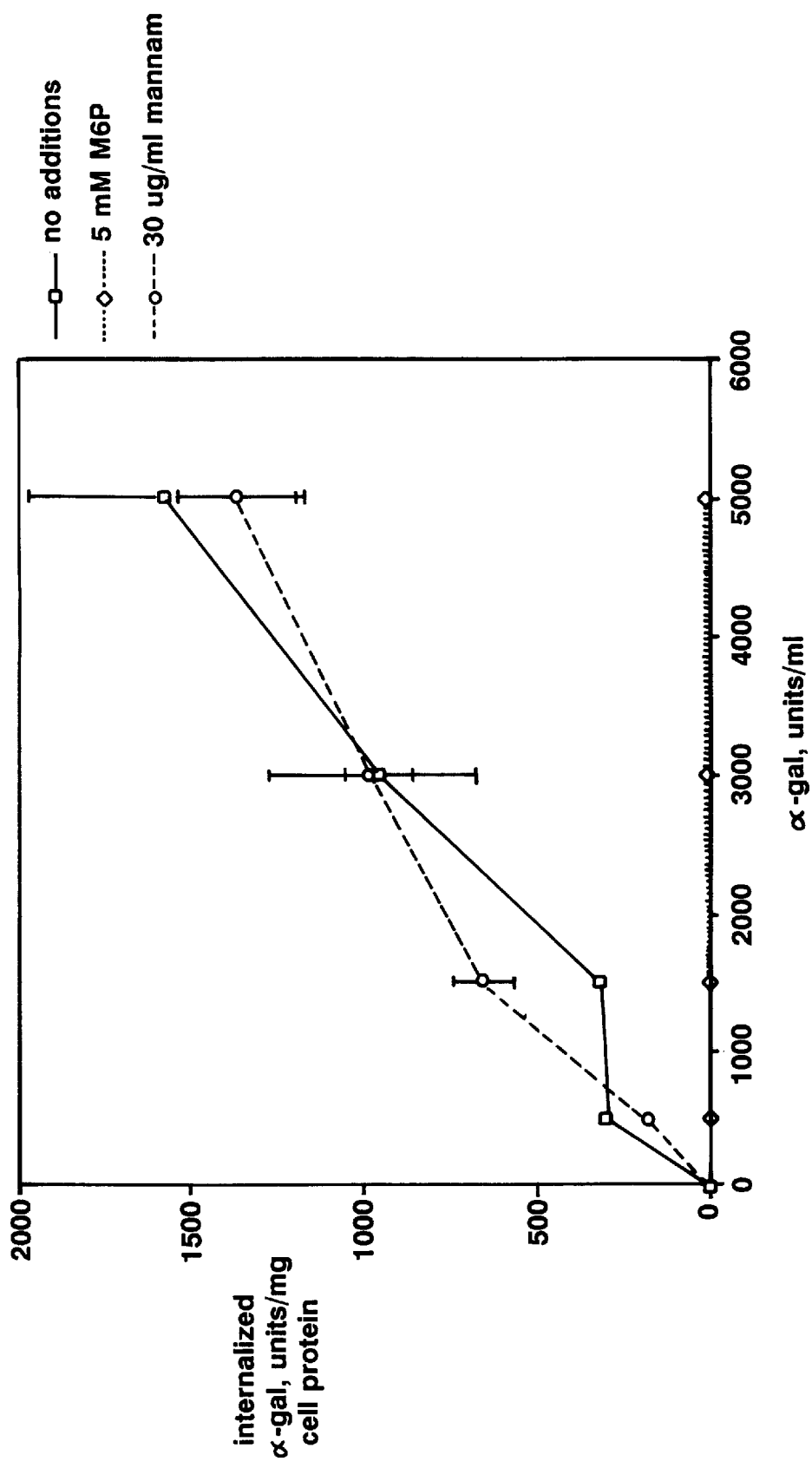
FIG. 7 is a line graph depicting internalization by Fabry fibroblasts of human α-gal A prepared in accordance with the invention. The intracellular α-gal A activity and total protein concentration were measured after incubation of the cells with increasing concentrations of human α-gal A prepared in accordance with the invention. The effects of the potential internalization-inhibitors mannose-6 phosphate (M6P; open diamonds) and mannan (open circles) are shown.

In order to demonstrate M6P-mediated internalization of α-gal A, skin fibroblasts from a Fabry disease patient (NIGMS Human Genetic Mutant Cell Repository) were cultured overnight in the presence of increasing concentrations of purified α-gal A of the invention. Some of the samples contained 5 mM soluble M6P, which competitively inhibits binding to, and as a result, internalization by, the mannose-6 phosphate receptor. Other samples contained 30 µg/ml mannan, which inhibits binding to, and as a result, internalization by, the mannose receptor. Following incubation, the cells were washed and harvested by scraping into lysis buffer (10 mM Tris, pH 7.2, 100 mM NaCl, 5 mM EDTA, 2 mM Pefabloc™ (Boehringer-Mannheim, Indianapolis, Ind.) and 1% NP-40). The lysed samples were then assayed for protein concentration and α-gal A activity. The results are expressed as units of α-gal A activity/mg cell protein. The Fabry cells internalized α-gal A in a dose-dependent manner (FIG. 7). This internalization was inhibited by mannose-6 phosphate, but there was no inhibition with mannan. Therefore, internalization of α-gal A in Fabry fibroblasts is mediated by the mannose-6 phosphate receptor, but not by the mannose receptor.

α-gal A is also internalized in vi tro by endothelial cells, important target cells for the treatment of Fabry disease. Human umbilical vein endothelial cells (HUVECs) were cultured overnight with 7500 units of α-gal A; some of the wells contained M6P. After the incubation period, cells were harvested and assayed for α-gal A as described above. The cells incubated with α-gal A only had enzyme levels almost 10-fold above those of control (no incubation with α-gal A) cells. M6P inhibited the intracellular accumulation of α-gal A, suggesting that the internalization of α-gal A by HUVECs is mediated by the M6P receptor. Thus, the human α-gal A of the invention is internalized by clinically relevant cells.

Few cultured human cell lines are known to express the mannose receptor. However, a mouse macrophage-like cell line (J774.E) which bears mannose receptors but few if any mannose 6-phosphate receptors can be used to determine whether purified α-gal A of the invention is internalized via the mannose receptor (Diment et al., J. Leukocyte Biol. 42:485–490, 1987). J774.E cells were cultured overnight in the presence of 10,000 units/ml α-gal A. Selected samples also contained 2 mM M6P, and others contained 100 µg/ml mannan. The cells were washed and harvested as described above, and the total protein and α-gal A activity of each sample was determined. The results are shown in Table 5. M6P does not inhibit the uptake of α-gal A by these cells, while mannan decreases the accumulated α-gal A levels by 75%. Thus, the α-gal A of the invention may be internalized by the mannose receptor in cell types that express this particular cell surface receptor.

TABLE 6

Internalization of α-Gal A by J774.E Cells
α-Gal A Activity (units/mg total protein)

| | No additions | + α-gal A | + α-gal A, + M6P | + α-gal A, + mannan |
|---|---|---|---|---|
| J774.E | 409 ± 25 | 6444 ± 554 | 6297 ± 674 | 1654 ± 323 |

[mannan] = 100 µg/ml
[M6P] = 2 mM or 660 µg/ml

These experiments demonstrate that the α-gal A produced by stably transfected human cells may be internalized by cells via the mannose or mannose-6-phosphate receptor.

G. Correction of Fabry Fibroblasts by Human Fibroblasts Expressing α-Gal A

Figure 8:
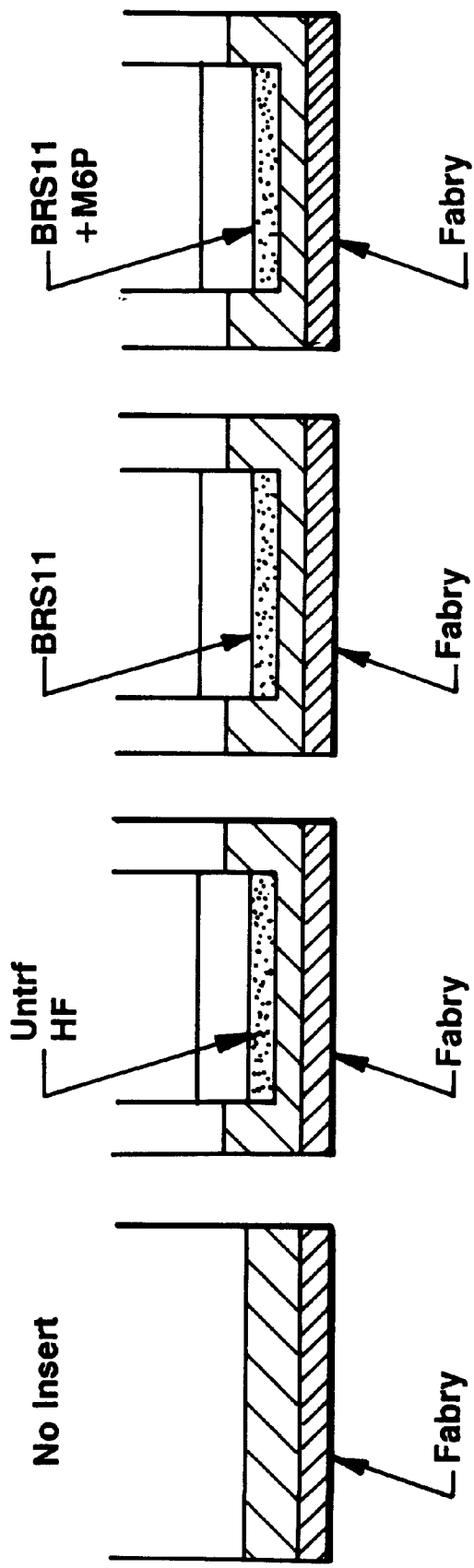
FIG. 8 is a schematic diagram of the experimental paradigm designed to examine Fabry fibroblasts following internalization of α-gal A. The α-gal A activity of the Fabry cells is measured after exposure to either normal or α-gal A-overexpressing human fibroblasts cultured in Transwell™ inserts. "M6P"=mannose-6 phosphate; "Untrf HF"= untransfected human fibroblasts; "BRS11"=a transfected, α-gal A-overexpressing fibroblast strain.

For gene therapy, an implant of autologous cells producing α-gal A must produce the enzyme in a form modified appropriately to "correct" the α-gal A deficiency in target cells. To assess the effect of α-gal A production by transfected human fibroblasts on Fabry cells, fibroblasts harvested from Fabry disease patients (NIGMS Human Genetics Mutant Cell Repository) were co-cultured with an α-gal A-producing cell strain (BRS-11) in Transwells® (Costar, Cambridge, Mass.). The experimental scheme is depicted in FIG. 8. Fabry cells were cultured in 12-well tissue culture dishes, some of which contained inserts (Transwells®, 0.4 µm pore size) having a surface on which cells can be grown. The growth matrix of the insert is porous and allows macromolecules to pass from the upper to the lower milieu. One set of inserts contained normal human foreskin (HF) fibroblasts, which secrete minimal levels of α-gal A, while another set contained the stably transfected human fibroblast strain, BRS-11, which secretes large amounts of α-gal A. In the wells co-cultured with α-gal A-producing cells, α-gal A can enter the medium bathing the Fabry cells, and potentially be internalized by the Fabry cells.

The data in Table 7 show that Fabry cells internalized the secreted α-gal A. The intracellular levels of α-gal A were monitored for three days. Those cells cultured alone (no insert) or in the presence of non-transfected foreskin fibroblasts (HF insert) had very low intracellular levels of α-gal A activity. The Fabry cells cultured with the α-gal A-producing (BRS-11 insert) cells, however, exhibited enzyme levels similar to those of normal cells by the end of Day 2 (normal fibroblasts have 25–80 units α-gal A/mg protein). That the correction is attributable to α-gal A taken up via the M6P receptor is demonstrated by its inhibition with mannose-6-phosphate (BRS-11 insert+M6P).

TABLE 7

Correction of Fabry Fibroblasts by Human Fibroblasts Expressing α-Gal A
α-Gal A Activity (units/mg total protein)

| Time | no insert | HF insert | BRS-11 insert | BRS-11 insert + M6P |
|---|---|---|---|---|
| Day 1 | 2 ± 1 | 2 ± 1 | 13 ± 1 | 4 ± 1 |
| Day 2 | 2 ± 1 | 2 ± 1 | 40 ± 11 | 6 ± 2 |
| Day 3 | 2 ± 1 | 5 ± 1 | 85 ± 1 | 9 ± 1 |

H. Utility of Other Cell Types

Other cell types can be used in the method described herein. The cells can be obtained from a variety of tissues and include all cell types that can be maintained in culture. For example, primary and secondary cells that can be transfected by the present method include human fibroblasts, keratinocytes, epithelial cells (e.g., mammary or intestinal epithelial cells), endothelial cells, glial cells, neural cells, formed elements of the blood (e.g., lymphocytes and bone marrow cells), muscle cells, and precursors of these somatic cell types. Fibroblasts are of particular interest. Primary cells are preferably obtained from the individual to whom the transfected primary or secondary cells are to be administered, so that they will not be rejected by the patient's immune system. However, if proper attention is paid to avoiding or suppressing immunorejection (as described below), cells of a human donor other than the patient can be used as well. This would permit use of cells from an standardized, established, stably transfected cell line in all patients.

I. Administration of α-Gal A-Expressing Cells

The cells described above may be introduced into an individual, through various standardized routes of administration, so that they will reside in, for example, the renal subcapsule, a subcutaneous compartment, the central nervous system, the intrathecal space, the liver, the intraperiotoneal cavity, or within a muscle. The cells may also be injected intravenously or intra-arterially so that they circulate within the individual's bloodstream. Once implanted in the individual, the transfected cells will produce and secrete the therapeutic product, glycosylated human α-gal A.

The number of genetically modified cells that will be introduced into the individual will vary, but can be determined by skilled artisans. The age, weight, sex, and general physical condition of each patient, as well as the volume of distribution, the half-life and bioavailability of the enzyme, and the in vivo productivity of the genetically modified cells, will be among the primary considerations in determining dosage and route of administration. Typically, between one million and one billion cells will be used, with expression levels ranging from 100–100,000 units per $10^6$ cells per day. If necessary, the procedure may be repeated or modified until the desired result, for example, relief from the symptoms associated with Fabry disease, is achieved.

As described above, the cells used will generally be patient-specific, i.e., obtained from the individual to whom the transfected primary or secondary cells are to be administered, so that they will not be rejected by the patient's immune system. If, however, this scenario is not possible or desirable, cells may be obtained from another individual, genetically modified as described herein, and implanted into the patient who is suffering from α-gal A deficiency.

The use of cells from an individual other than the recipient might require administration of an immunosuppressant, alteration of histocompatibility antigens, or use of a barrier device to prevent rejection of the implanted cells. The barrier device will be made of a material (e.g., a membrane such as XM-50 from Amicon, Beverly, Mass.) that permits the secreted product to pass into the recipient's circulation or tissues, but prevents contact between the implanted cells and the recipient's immune system, and thus prevents an immune response to (and possible rejection of) the cells by the recipient. For further guidance regarding gene therapy, see Selden et al. (WO 93/09222).

The cells may alternatively be embedded in a matrix or gel material, such as described in co-owned U.S. Ser. No. 08/548,002, which describes the use of hybrid matrix implants, or in Jain et al. (PCT application WO 95/19430), which describes macroencapsulation of secretory cells in a hydrophilic gel material (each of which is hereby incorporated by reference).

J. Pharmaceutical Formulation for Conventional Administration of α-Gal A Protein The α-gal A protein that is expressed and secreted by stably transfected (or otherwise genetically modified) human cells and purified as described herein may be administered to individuals who produce insufficient or defective α-gal A protein. The protein may be administered in a pharmaceutically acceptable carrier, at a pH below 6.5, e.g. in a formulation as described in Example III. Examples of excipients which may be included with the formulation are buffers such as citrate buffer, phosphate buffer, acetate buffer, and bicarbonate buffer, amino acids, urea, alcohols, ascorbic acid, phospholipids, proteins, such as serum albumin and gelatin, EDTA, sodium chloride, liposomes, polyvinylpyrollidone, mannitol, sorbitol, glycerol, propylene glycol and polyethylene glycol (e.g., PEG-4000, PEG-6000). The route of administration may be, for example, intravenous, intra-arterial, subcutaneous, intraperitoneal, intracerebral, intramuscular, intrapulmonary, or transmucosal. The route of administration and the amount of protein delivered will be determined by factors that are well within the ability of skilled artisans to assess. Furthermore, skilled artisans are aware that the route of administration and dosage of a therapeutic protein may be varied for a given patient until a therapeutic dosage level is obtained. Typically, doses of α-gal A of 0.01–100 mg/kg of body weight will be administered. It is expected that regularly repeated doses of the protein will be necessary over the life of the patient.

K. Treatment of Other Conditions Caused by Enzyme Deficiencies

It is likely that other conditions caused by deficiencies in lysosomal storage enzymes other than α-gal A will be amenable to treatment by methods comparable to those described herein. In these cases, DNA which encodes a functional form of the deficient enzyme would be substituted Lor the DNA encoding α-gal A in the expression constructs disclosed herein. Examples of enzyme deficiency syndromes that have been identified, and that may be amenable to treatment as described herein, are shown in Table 8. The information in this Table is taken from E. Neufeld (Ann. Rev. Biochem. 60:257–280, 1991), which is hereby incorporated by reference.

TABLE 8

Summary of Lysosomal Storage Disorders

| Disorder | Primary deficiency [secondary deficiency] |
| --- | --- |
| Disorders of sphingolipid degradation | |
| Fabry disease | α-galactosidase |
| Farber disease | ceramidase |
| Gaucher disease | glucocerebrosidase |
| $G_{M1}$ gangliosidosis | β-galactosidase |
| $G_{M2}$ gangliosidoses | |
| Tay-Sachs disease | β-hexosaminidase, α-subunit [hexosaminidase A] |
| Sandhoff disease | β-hexosaminidase, β-subunit [hexosaminidases A and B] |
| Activator deficiency | $G_{M2}$ activator |
| Krabbe disease | galactosylceramidase |

TABLE 8-continued

Summary of Lysosomal Storage Disorders

| Disorder | Primary deficiency [secondary deficiency] |
|---|---|
| Metachromatic leukodystrophy | |
| enzyme-deficient form | arylsulfatase A |
| activator-deficient form | sulfatide activator/saposin |
| Mucolipidosis IV | primary defect unknown [ganglioside sialidase] |
| Multiple sulfatase deficiency | primary defect unknown [deficiency of all sulfatases] |
| Niemann-Pick disease | sphingomyelinase |
| Schindler disease | α-N-acetylgalactosaminidase |
| Disorders of glycoprotein degradation | |
| Aspartylglycosaminuria | aspartylglycosaminidase |
| Fucosidosis | α-L-fucosidase |
| Galactosialidosis | protective protein/cathepsin β-galactosidase and sialidase] |
| α-Mannosidosis | α-mannosidase |
| β-Mannosidosis | β-mannosidase |
| Sialidosis | sialidase |
| Disorders of glycosaminoglycan degradation | |
| Hunter syndrome | iduronate sulfatase |
| Hurler and Scheie syndromes | α-L-iduronidase |
| Maroteaux-Lamy syndrome | GalNAc 4-sulfatase/ arylsulfatase |
| Morquio syndrome | |
| A-subtype | Gal 6-sulfatase |
| B-subtype | β-galactosidase |
| Sanfilippo syndrome | |
| A-subtype | heparan N-sulfatase |
| B-subtype | α-N-acetylglucosaminidase |
| C-subtype | AcetylCoA: glucosamine N-acetyltransferase |
| D-subtype | GlcNAc 6-sulfatase |
| Sly syndrome | β-glucuronidase |
| Other single enzyme deficiency disorders | |
| Pompe disease (glycogenosis II) | α-glucosidase |
| Wolman disease | acid lipase |
| Disorders of lysosomal enzyme biosynthesis | |
| I-cell disease and pseudoHurler polydystrophy | 6-phospho-N-acetyl-glucosamine transferase [mislocalization of many lysosomal enzymes] |
| Disorders of lysosmal membrane transport | |
| Cystinosis | cystine transport |
| Sialic storage and Salla disease | sialic acid transport |

V. Other Embodiments

The invention described herein has been exemplified in part by methods of treatment that employ cells which express a particular gene product following transfection, i.e., after introduction of a construct encoding the gene product and having regulatory elements that control expression of the coding sequence. These methods may also be carried out using cells that have been genetically modified by other procedures, including gene targeting and gene activation (see Treco et al. (WO 95/31560, herein incorporated by reference; see also Selden et al. WO 93/09222).

The hGH signal peptide can be used with heterologous proteins other than α-gal A, to increase the level of expression and secretion of the heterologous protein. Examples of such proteins include α-1 antitrypsin, antithrombin III, apolipoprotein E, apolipoprotein A-1, blood clotting factors V, VII, VIII, IX, X, and XIII, bone growth factor-2, bone growth factor-7, calcitonin, catalytic antibodies, DNAse, erythropoietin, FSH-β, globins, glucagon, glucocerebrosidase, G-CSF, GM-CSF, growth hormone, immune response modifiers, immunoglobulins, insulin, insulinotropin, insulin-like growth factors, interferon-β, interferon-β nerve growth factors, interleukin-1, interleukin-2, interleukin-3, interleukin-4, interleukin-6, interleukin-11, interleukin-12, IL-2 receptor, IL-1 receptor antagonists, low density lipoprotein receptor, M-CSF, parathyroid hormone, protein kinase C, soluble CD4, superoxide dismutase, tissue plasminogen activator, TGF-β, tumor necrosis factor, TSHβ, tyrosine hydroxylase, and urokinase.

Other embodiments are within the following claims.

What is claimed is:

1. A DNA molecule comprising a first sequence encoding the hGH signal peptide (SEQ ID NO:21), said first sequence comprising an intron; and, linked to the 3' end of the first sequence, a second sequence encoding a polypeptide comprising human α-gal A.

2. The DNA molecule of claim 1, further comprising a 3' untranslated sequence comprising a polyadenylation site.

3. An expression construct comprising the DNA molecule of claim 1 and suitable for expression in a human cell.

4. A cultured human cell containing a DNA molecule that (a) encodes a polypeptide comprising human α-gal A linked to an heterologous signal peptide, and (b) permits expression of the polypeptide in the cell.

5. The cell of claim 4, said cell being a fibroblast.

6. The cell of claim 4, wherein said cell is selected from the group consisting of an epithelial cell, an endothelial cell, a bone marrow cell, a glial cell, a hepatocyte, a keratinocyte, a myocyte, a neuron, or a precursor of these cell types.

7. The cell of claim 4, wherein said signal peptide is the hGH signal peptide (SEQ ID NO:21).

8. The cultured human cell of claim 4, wherein the DNA is introduced into the cell, or a precursor of the cell, by liposome-mediated transfection, polybrene-mediated transfection, DEAE dextran-mediated transfection, electroporation, calcium phosphate precipitation, microinjection, or velocity driven microprojectiles.

9. A clonal cell strain of cultured human cells transfected with a DNA molecule that (a) encodes a polypeptide comprising human α-gal A linked to an heterologous signal peptide, and (b) permits expression of the polypeptide in the cells.

10. The clonal cell strain of claim 9, said cells being fibroblasts.

11. The clonal cell strain of claim 9, wherein the strain is descended from a cell that was transfected with the DNA molecule by liposome-mediated transfection, polybrene-mediated transfection, DEAE dextran-mediated transtection, electroporation, calcium phosphate precipitation, microinjection, or velocity driven microprojectiles.

12. A clonal cell line of immortalized human cells transfected with a DNA molecule that (a) encodes a polypeptide comprising human α-gal A linked to an heterologous signal peptide, and (b) permits expression of the polypeptide in the cells.

13. The clonal cell line of claim 12, wherein said cells are selected from the group consisting of Bowes melanoma cells, Daudi cells, HeLa cells, HL-60 cells, HT1080 cells, Jurkat cells, KB carcinoma cells, K-562 leukemia cells, MCF-7 breast cancer cells, MOLT-4 cells, Namalwa cells, Raji cells, RPMI 8226 cells, U-937 cells, WI-38VA13 (subline 2R4) cells, and 2780AD ovarian carcinoma cells.

14. The clonal cell line of claim 12, wherein the cell line is descended from a cell that was transfected with the DNA molecule by liposome-mediated transfection, polybrene-mediated transfection, DEAE dextran-mediated transfection, electroporation, calcium phosphate precipitation, microinjection, or velocity driven microprojectiles.

15. A protein comprising (a) the hGH signal peptide (SEQ ID NO:21) linked by a peptide bond to (b) human α-gal A.

16. A process for making glycosylated human α-gal A, comprising
culturing the cell of claim 5, under conditions permitting expression of human α-gal A from said DNA molecule and secretion of glycosylated human α-gal A into the culture medium of the cell; and
isolating glycosylated human α-gal A from the culture medium.

17. A process for making glycosylated human α-gal A, comprising
culturing the cell of claim 12 under conditions permitting expression of human α-gal A from said DNA molecule and secretion of glycosylated human α-gal A into the culture medium of the cell; and
isolating glycosylated human α-gal A from the culture medium.

18. A method for making glycosylated human α-gal A, comprising culturing a human cell containing a DNA molecule that encodes a polypeptide comprising human α-gal A and a heterologous signal peptide under conditions permitting expression of human α-gal A from said DNA molecule.

19. The cell of claim 4, wherein said cell is an epithelial cell.

20. The cell of claim 4, wherein said cell is a bone marrow cell.

21. The cell of claim 4, wherein said cell is a keratinocyte.

22. The cell of claim 4, wherein said cell is a myocyte.

23. The clonal cell line of claim 12, wherein said cells are Ht1080 cells.

24. The clonal cell line of claim 12, wherein said cells are K-562 leukemia cells.

25. The clonal cell line of claim 12, wherein said cells are U-937 cells.

26. The cultured human cell of claim 4, wherein the DNA is introduced into the cell, or a precursor of the cell, by liposome-mediated transfection.

27. The cultured human cell of claim 4, wherein the DNA is introduced into the cell, or a precursor of the cell, by electroporation.

28. The cultured human cell of claim 4, wherein the DNA is introduced into the cell, or a precursor of the cell, by calcium phosphate precipitation.

29. The cultured human cell of claim 4, wherein the DNA is introduced into the cell, or a precursor of the cell, by microinjection.

30. The clonal cell strain of claim 9, wherein the strain is descended from a cell that was transfected with the DNA molecule by liposome-mediated transfection.

31. The clonal cell strain of claim 9, wherein the strain is descended from a cell that was transfected with the DNA molecule by electroporation.

32. The clonal cell strain of claim 9, wherein the strain is descended from a cell that was transfected with the DNA molecule by calcium phosphate precipitation.

33. The clonal cell strain of claim 9, wherein the strain is descended from a cell that was transfected with the DNA molecule by microinjection.

34. The clonal cell line of claim 12, wherein the cell line is descended from a cell that was transfected with the DNA molecule by liposome-mediated transfection.

35. The clonal cell line of claim 12, wherein the cell line is descended from a cell that was transfected with the DNA molecle by electroporation.

36. The clonal cell line of claim 12, wherein the cell line is descended from a cell that was transfected with the DNA molecule by calcium phosphate prescription.

37. The clonal cell line of claim 12, wherein the cell line is descended from a cell that was transfected with the DNA molecule by microinjection.

* * * * *

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO:1:

CTGGGCTGTA GCTATGATAA AC      22

(2) INFORMATION FOR SEQ ID NO:2:

```
    (i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO:2:

TCTAGCTGAA GCAAAACAGT G                                          21

(2) INFORMATION FOR SEQ ID NO:3:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (xi) SEQUENCE DESCRIPTION: SEQ ID NO:3:

ATTGGTCCGC CCCTGAGGT                                             19

(2) INFORMATION FOR SEQ ID NO:4:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:4:

TGATGCAGGA ATCTGGCTCT                                            20

(2) INFORMATION FOR SEQ ID NO:5:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:5:

TTTTGGATCC ACCATGGCTA                                            20

(2) INFORMATION FOR SEQ ID NO:6:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:6:

TTTTGCCGGC ACTGCCCTCT TGAA                                       24

(2) INFORMATION FOR SEQ ID NO:7:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:7:

TTTTCAGCTG GACAATGGAT TGGC                                       24

(2) INFORMATION FOR SEQ ID NO:8:

(i) SEQUENCE CHARACTERISTICS:
```

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

TTTTGCTAGC TGGCGAATCC                                                      20

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

TTTTGGATCC GTGTCCCATA GTGTTTCCAA                                            30

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:10:

TTTTGGATCC GCAGTCGTGG CCAGTACC                                              28

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:11:

CTAGTCCTAG GA                                                               12

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

TTTTGAGCAC AGAGCCTCGC CT                                                    22

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:13:

TTTTGGATCC GGTGAGCTGC GAGAATAGCC                                            30

(2) INFORMATION FOR SEQ ID NO:14:

(i) SEQUENCE CHARACTERISTICS:
        (A) LENGTH: 76 base pairs (B) TYPE: nucleic acid
        (C) STRANDEDNESS: single
        (D) TOPOLOGY: linear (xi) SEQUENCE DESCRIPTION: SEQ ID NO:14:

GGGCCCCCAG CCCCAGCCCT CCCATTGGTG GAGGCCCTTT TGGAGGCACC CTAGGGCCAG    60

GAAACTTTTG CCGTAT    76

(2) INFORMATION FOR SEQ ID NO:15:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:15:

AAATAGGGCA GATCCGGGCT TTATTATTTT AGCACCACGG CCGCCGAGAC CGCGTCCGCC    60

CCGCGAGCA    69

(2) INFORMATION FOR SEQ ID NO:16:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:16:

TGCCCTATTT ATACGGCAAA AGTTTCCTGG CCCTAGGGTG CCTCCAAAAG GGCCTCCACC    60

AATGGGAGGG CTGGGGCTGG GGGCCC    86

(2) INFORMATION FOR SEQ ID NO:17:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:17:

CGCGGGGCGG ACGCGGTCTC GGCGGCCGTG GTGCTAAAAT AATAAAGCCC GGATC    55

(2) INFORMATION FOR SEQ ID NO:18:

(i) SEQUENCE CHARACTERISTICS:
        (A) LENGTH: 1343 base pairs
        (B) TYPE: nucleic acid
        (C) STRANDEDNESS: single
        (D) TOPOLOGY: linear (xi) SEQUENCE DESCRIPTION: SEQ ID NO:18:

CCGCGGGAAA TTTATGCTGT CCGGTCACCG TGACAATGCA GCTGAGGAAC CCAGAACTAC    60

ATCTGGGCTG CGCGCTTGCG CTTCGCTTCC TGGCCCTCGT TTCCTGGGAC ATCCCTGGGG   120

CTAGAGCACT GGACAATGGA TTGGCAAGGA CGCCTACCAT GGGCTGGCTG CACTGGGAGC   180

GCTTCATGTG CAACCTTGAC TGCCAGGAAG AGCCAGATTC CTGCATCAGT GAGAAGCTCT   240

TCATGGAGAT GGCAGAGCTC ATGGTCTCAG AAGGCTGGAA GGATGCAGGT TATGAGTACC   300

TCTGCATTGA TGACTGTTGG ATGGCTCCCC AAAGAGATTC AGAAGGCAGA CTTCAGGCAG   360

ACCCTCAGCG CTTTCCTCAT GGGATTCGCC AGCTAGCTAA TTATGTTCAC AGCAAAGGAC   420

TGAAGCTAGG GATTTATGCA GATGTTGGAA ATAAAACCTG CGCAGGCTTC CCTGGGAGTT   480

```
TTGGATACTA CGACATTGAT GCCCAGACCT TGCTGACTG GGGAGTAGAT CTGCTAAAAT    540

TTGATGGTTG TTACTGTGAC AGTTTGGAAA ATTTGGCAGA TGGTTATAAG CACATGTCCT    600

TGGCCCTGAA TAGGACTGGC AGAAGCATTG TGTACTCCTG TGAGTGGCCT CTTTATATGT    660

GGCCCTTTCA AAAGCCCAAT TATACAGAAA TCCGACAGTA CTGCAATCAC TGGCGAAATT    720

TTGCTGACAT TGATGATTCC TGGAAAAGTA TAAAGAGTAT CTTGGACTGG ACATCTTTTA    780

ACCAGGAGAG AATTGTTGAT GTTGCTGGAC CAGGGGGTTG GAATGACCCA GATATGTTAG    840

TGATTGGCAA CTTTGGCCTC AGCTGGAATC AGCAAGTAAC TCAGATGGCC CTCTGGGCTA    900

TCATGGCTGC TCCTTTATTC ATGTCTAATG ACCTCCGACA CATCAGCCCT CAAGCCAAAG    960

CTCTCCTTCA GGATAAGGAC GTAATTGCCA TCAATCAGGA CCCCTTGGGC AAGCAAGGGT   1020

ACCAGCTTAG ACAGGGAGAC AACTTTGAAG TGTGGGAACG ACCTCTCTCA GGCTTAGCCT   1080

GGGCTGTAGC TATGATAAAC CGGCAGGAGA TTGGTGGACC TCGCTCTTAT ACCATCGCAG   1140

TTGCTTCCCT GGGTAAAGGA GTGGCCTGTA ATCCTGCCTG CTTCATCACA CAGCTCCTCC   1200

CTGTGAAAAG GAAGCTAGGG TTCTATGAAT GGACTTCAAG GTTAAGAAGT CACATAAATC   1260

CCACAGGCAC TGTTTTGCTT CAGCTAGAAA ATACAATGCA GATGTCATTA AAAGACTTAC   1320

TTTAAAAAAA AAAAAAACTC GAG                                          1343

(2) INFORMATION FOR SEQ ID NO:19:

(i) SEQUENCE CHARACTERISTICS:
        (A) LENGTH: 210 base pairs
        (B) TYPE: nucleic acid
        (C) STRANDEDNESS: single
        (D) TOPOLOGY: linear (xi) SEQUENCE DESCRIPTION: SEQ ID NO:19:

CTGGGCTGTA GCTATGATAA ACCGGCAGGA GATTGGTGGA CCTCGCTCTT ATACCATCGC     60

AGTTGCTTCC CTGGGTAAAG GAGTGGCCTG TAATCCTGCC TGCTTCATCA CACAGCTCCT    120

CCCTGTGAAA AGGAAGCTAG GGTTCTATGA ATGGACTTCA AGGTTAAGAA GTCACATAAA    180

TCCCACAGGC ACTGTTTTGC TTCAGCTAGA                                     210

(2) INFORMATION FOR SEQ ID NO:20:

(i) SEQUENCE CHARACTERISTICS:
        (A) LENGTH: 268 base pairs
        (B) TYPE: nucleic acid
        (C) STRANDEDNESS: single
        (D) TOPOLOGY: linear (xi) SEQUENCE DESCRIPTION: SEQ ID NO:20:

ATTGGTCCGC CCCTGAGGTT AATCTTAAAA GCCCAGGTTA CCCGCGGAAA TTTATGCTGT     60

CCGGTCACCG TGACAATGCA GCTGAGGAAC CCAGAACTAC ATCTGGGCTG CGCGCTTGCG    120

CTTCGCTTCC TGGCCCTCGT TTCCTGGGAC ATCCCTGGGG CTAGAGCACT GGACAATGGA    180

TTGGCAAGGA CGCCTACCAT GGGCTGGCTG CACTGGGAGC GCTTCATGTG CAACCTTGAC    240

TGCCAGGAAG AGCCAGATTC CTGCATCA                                       268

(2) INFORMATION FOR SEQ ID NO:21:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: linear
```

(ii) MOLECULE TYPE: peptide (xi) SEQUENCE DESCRIPTION: SEQ ID NO:21:

Met Ala Thr Gly Ser Arg Thr Ser Leu Leu Leu Ala Phe Gly Leu Leu
1               5                  10                  15

Cys Leu Pro Trp Leu Gln Glu Gly Ser Ala
            20                  25

(2) INFORMATION FOR SEQ ID NO:22:

(i) SEQUENCE CHARACTERISTICS:
            (A) LENGTH: 78 base pairs
            (B) TYPE: nucleic acid
            (C) STRANDEDNESS: single
            (D) TOPOLOGY: linear (xi) SEQUENCE DESCRIPTION: SEQ ID NO:22:

ATGGCTACAG GCTCCCGGAC GTCCCTGCTC CTGGCTTTTG GCCTGCTCTG CCTGCCCTGG        60

CTTCAAGAGG GCAGTGCC        78

(2) INFORMATION FOR SEQ ID NO:23:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:23:

TTTTGGATCC CTCGAGGACA TTGATTATTG ACTAG        35

(2) INFORMATION FOR SEQ ID NO:24:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:24:

TTTTGGATCC CGTGTCAAGG ACGGTGAC        28

(2) INFORMATION FOR SEQ ID NO:25:

(i) SEQUENCE CHARACTERISTICS:
            (A) LENGTH: 1197 base pairs
            (B) TYPE: nucleic acid
            (C) STRANDEDNESS: single
            (D) TOPOLOGY: linear (xi) SEQUENCE DESCRIPTION: SEQ ID NO:25:

CTGGACAATG GATTGGCAAG GACGCCTACC ATGGGCTGGC TGCACTGGGA GCGCTTCATG        60

TGCAACCTTG ACTGCCAGGA AGAGCCAGAT TCCTGCATCA GTGAGAAGCT CTTCATGGAG        120

ATGGCAGAGC TCATGGTCTC AGAAGGCTGG AAGGATGCAG GTTATGAGTA CCTCTGCATT        180

GATGACTGTT GGATGGCTCC CCAAAGAGAT TCAGAAGGCA GACTTCAGGC AGACCCTCAG        240

CGCTTTCCTC ATGGGATTCG CCAGCTAGCT AATTATGTTC ACAGCAAAGG ACTGAAGCTA        300

GGGATTTATG CAGATGTTGG AAATAAAACC TGCGCAGGCT TCCCTGGGAG TTTTGGATAC        360

TACGACATTG ATGCCCAGAC CTTTGCTGAC TGGGGAGTAG ATCTGCTAAA ATTTGATGGT        420

TGTTACTGTG ACAGTTTGGA AAATTTGGCA GATGGTTATA AGCACATGTC CTTGGCCCTG        480

-continued

```
AATAGGACTG GCAGAAGCAT TGTGTACTCC TGTGAGTGGC CTCTTTATAT GTGGCCCTTT     540

CAAAAGCCCA ATTATACAGA AATCCGACAG TACTGCAATC ACTGGCGAAA TTTTGCTGAC     600

ATTGATGATT CCTGGAAAAG TATAAAGAGT ATCTTGGACT GGACATCTTT TAACCAGGAG     660

AGAATTGTTG ATGTTGCTGG ACCAGGGGGT TGGAATGACC CAGATATGTT AGTGATTGGC     720

AACTTTGGCC TCAGCTGGAA TCAGCAAGTA ACTCAGATGG CCCTCTGGGC TATCATGGCT     780

GCTCCTTTAT TCATGTCTAA TGACCTCCGA CACATCAGCC CTCAAGCCAA AGCTCTCCTT     840

CAGGATAAGG ACGTAATTGC CATCAATCAG GACCCCTTGG GCAAGCAAGG GTACCAGCTT     900

AGACAGGGAG ACAACTTTGA AGTGTGGAA  CGACCTCTCT CAGGCTTAGC CTGGGCTGTA     960

GCTATGATAA ACCGGCAGGA GATTGGTGGA CCTCGCTCTT ATACCATCGC AGTTGCTTCC    1020

CTGGGTAAAG GAGTGGCCTG TAATCCTGCC TGCTTCATCA CACAGCTCCT CCCTGTGAAA    1080

AGGAAGCTAG GGTTCTATGA ATGGACTTCA AGGTTAAGAA GTCACATAAA TCCCACAGGC    1140

ACTGTTTTGC TTCAGCTAGA AAATACAATG CAGATGTCAT TAAAAGACTT ACTTTAA      1197
```

(2) INFORMATION FOR SEQ ID NO:26:

(i) SEQUENCE CHARACTERISTICS:
        (A) LENGTH: 398 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:26:

```
Leu Asp Asn Gly Leu Ala Arg Thr Pro Thr Met Gly Trp Leu His Trp
 1               5                  10                  15

Glu Arg Phe Met Cys Asn Leu Asp Cys Gln Glu Glu Pro Asp Ser Cys
             20                  25                  30

Ile Ser Glu Lys Leu Phe Met Glu Met Ala Glu Leu Met Val Ser Glu
         35                  40                  45

Gly Trp Lys Asp Ala Gly Tyr Glu Tyr Leu Cys Ile Asp Asp Cys Trp
     50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                 85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
    210                 215                 220
```

```
Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
370                 375                 380

Gln Leu Glu Asn Thr Met Gln Met Ser Leu Lys Asp Leu Leu
385                 390                 395
```

(2) INFORMATION FOR SEQ ID NO:27:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (xi) SEQUENCE DESCRIPTION: SEQ ID NO:27:

```
ATGGCTACAG GTAAGCGCCC CTAAAATCCC TTTGGGCACA ATGTGTCCTG AGGGGAGAGG      60

CAGCGACCTG TAGATGGGAC GGGGGCACTA ACCCTCAGGT TTGGGGCTTC TGAATGTGAG     120

TATCGCCATG TAAGCCCAGT ATTTGGCCAA TCTCAGAAAG CTCCTGGTCC CTGGAGGGAT     180

GGAGAGAGAA AAACAAACAG CTCCTGGAGC AGGGAGAGTG CTGGCCTCTT GCTCTCCGGC     240

TCCCTCTGTT GCCCTCTGGT TTCTCCCCAG GCTCCCGGAC GTCCCTGCTC CTGGCTTTTG     300

GCCTGCTCTG CCTGCCCTGG CTTCAAGAGG GCAGTGCC                             338
```

(2) INFORMATION FOR SEQ ID NO:28:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:28:

```
Leu Asp Asn Gly Leu Ala Arg Thr Pro Thr
1               5                   10
```